United States Patent [19]

Schaper et al.

[11] Patent Number: 5,859,009
[45] Date of Patent: Jan. 12, 1999

[54] SUBSTITUTED SPIROALKYLAMINO AND ALKOXY HETEROCYCLES, PROCESSES FOR THEIR PREPARATION, AND THEIR USE AS PESTICIDES AND FUNGICIDES

[75] Inventors: Wolfgang Schaper, Diedorf; Rainer Preuss, Berlin; Peter Braun, Nieder-Olm; Manfred Kern, Lörzweiler; Werner Knauf, Eppstein; Burkhard Sachse, Kelkheim; Ulrich Sanft, Hofheim; Anna Waltersdorfer, Frankfurt; Werner Bonin, Kelkheim; Adolf Linkies, Frankfurt; Dieter Bernd Reuschling, Butzbach, all of Germany

[73] Assignee: Hoechst Schering AgrEvo GmbH, Berlin, Germany

[21] Appl. No.: 540,987

[22] Filed: Oct. 11, 1995

[30] Foreign Application Priority Data

Oct. 13, 1994 [DE] Germany .............. 44 36 509.8

[51] Int. Cl.⁶ .................. C07D 405/12; C09K 3/10; A01N 43/40; C10M 133/40
[52] U.S. Cl. .................. 514/229.2; 514/230.5; 514/249; 514/250; 514/256; 514/258; 514/269; 544/229; 544/230; 544/253; 544/283; 544/278; 544/280; 544/295; 544/296; 544/299; 544/279; 252/47; 252/380; 106/12
[58] Field of Search .................. 544/326, 229, 544/230, 253, 283, 278, 280, 295, 296, 299, 279; 1/319, 269; 514/256, 229.2, 230.5, 234.5, 249, 250, 258; 47/57.6; 252/47, 380; 106/12

[56] References Cited

FOREIGN PATENT DOCUMENTS

| | | |
|---|---|---|
| 0519211 | 12/1992 | European Pat. Off. . |
| WO 93/19050 | 9/1993 | European Pat. Off. . |
| WO 93/05050 | 3/1993 | WIPO . |
| WO 95/07890 | 3/1995 | WIPO . |
| WO 95/07891 | 3/1995 | WIPO . |

Primary Examiner—Mark L. Berch
Assistant Examiner—Bruck Kifle
Attorney, Agent, or Firm—Frommer Lawrence & Haug LLP

[57] ABSTRACT

Substituted spiroalkylamino and -alkoxy heterocycles, processes for their preparation, and their use as pesticides and fungicides The invention relates to compounds of the formula

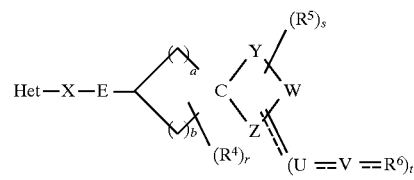

in which Het is optionally substituted 4-pyridyl or 4-pyrimidinyl; X is NH, O or $S(O)_{0-2}$; E is a bond or alkanediyl; Y and Z are $CH_2$, O and/or $S(O)_{0-2}$; W is $(CH_2)_{0-4}$; $R^4$ and $R^5$ are halogen, (halo)alkyl, (halo)alkoxy or alkylthio; r and s are 0-2; U is a bond, O, $S(O)_{0-2}$ or optionally substituted imino; and V is a bond CO, $SO_2$, —CQ—T— or —CT=N—; or U+V together are a double bond; and $R^6$ is as defined in the description. The invention furthermore relates to processes for their preparation and to their use as pesticides and fungicides.

20 Claims, No Drawings

SUBSTITUTED SPIROALKYLAMINO AND ALKOXY HETEROCYCLES, PROCESSES FOR THEIR PREPARATION, AND THEIR USE AS PESTICIDES AND FUNGICIDES

The invention relates to novel substituted spiroalkylamino and -alkoxy nitrogen heterocycles, to processes for their preparation, and to their use as pesticides and fungicides.

It has already been disclosed that certain spiroalkylamino- and -alkoxypyrimidines have fungicidal, acaricidal and insecticidal action (DE-A-4208254). However, the biological action of these compounds is not satisfactory in all fields of application, in particular when low rates and concentrations are applied.

There have now been found novel substituted spiroalkylamino and -alkoxy nitrogen heterocycles of the formula I

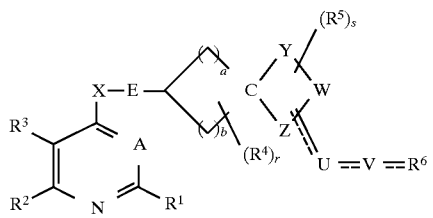

in which

R$^1$ is hydrogen, halogen, ($C_1$–$C_4$)-alkyl, ($C_1$–$C_4$)-haloalkyl, ($C_3$–$C_5$)-cycloalkyl or ($C_3$–$C_5$)-halocycloalkyl;

R$^2$ and R$^3$ are identical or different and are in each case hydrogen, ($C_1$–$C_4$)-alkyl, ($C_1$–$C_4$)-haloalkyl, ($C_2$–$C_4$)-alkenyl, ($C_2$–$C_4$)-haloalkenyl, ($C_2$–$C_4$)-alkynyl, ($C_2$–$C_4$)-haloalkynyl, tri-($C_1$–$C_4$)-alkylsilyl-($C_2$–$C_4$)-alkynyl, ($C_1$–$C_4$)-alkoxy, ($C_1$–$C_4$)-haloalkoxy, ($C_1$–$C_4$)-alkoxy-($C_1$–$C_4$)-alkyl, ($C_1$–$C_4$)-haloalkoxy-($C_1$–$C_4$)-alkyl, ($C_1$–$C_4$)-alkoxy-($C_1$–$C_4$)-haloalkyl, ($C_1$–$C_4$)-haloalkoxy-($C_1$–$C_4$)-haloalkyl, halogen, hydroxyl, ($C_1$–$C_4$)-hydroxyalkyl, ($C_1$–$C_4$)-alkanoyl, ($C_1$–$C_4$)-alkanoyl-($C_1$–$C_4$)-alkyl, ($C_1$–$C_4$)-haloalkanoyl, ($C_3$–$C_5$)-cycloalkyl, ($C_3$–$C_5$)-halocycloalkyl, cyano, ($C_1$–$C_4$)-cyanoalkyl, nitro, ($C_1$–$C_4$)-nitroalkyl, thiocyano, ($C_1$–$C_4$)-thiocyanoalkyl, ($C_1$–$C_4$)-alkoxycarbonyl, ($C_1$–$C_4$)-alkoxycarbonyl-($C_1$–$C_4$)-alkyl, ($C_1$–$C_4$)-haloalkoxycarbonyl, ($C_1$–$C_4$)-alkylthio, ($C_1$–$C_4$)-alkylthio-($C_1$–$C_4$)-alkyl, ($C_1$–$C_4$)-haloalkylthio, ($C_1$–$C_4$)-alkylsulfinyl, ($C_1$–$C_4$)-haloalkylsulfinyl, ($C_1$–$C_4$)-alkylsulfonyl or ($C_1$–$C_4$)-haloalkylsulfonyl; or R$^2$ and R$^3$ together with the carbon atoms to which they are bonded form an unsaturated 5- or 6-membered isocyclic ring which, if it is a 5-membered ring, can contain an oxygen or sulfur atom in place of $CH_2$ or which, if it is a 6-membered ring, can contain one or two nitrogen atoms in place of one or two CH units, and which is optionally substituted by 1, 2 or 3 identical or different radicals, these radicals being ($C_1$–$C_4$)-alkyl, ($C_1$–$C_4$)-haloalkyl, preferably trifluoromethyl, halogen, ($C_1$–$C_4$)-alkoxy or ($C_1$–$C_4$)-haloalkoxy, or R$^2$ and R$^3$ together with the carbon atoms to which they are bonded form a saturated 5-, 6- or 7-membered isocyclic ring which can contain oxygen and/or sulfur in place of one or two $CH_2$ groups and which is optionally substituted by 1, 2 or 3 ($C_1$–$C_4$)-alkyl groups;

A is CH or N;

X is NH, oxygen or $S(O)_q$ where q is 0, 1 or 2;

E is a direct bond or a straight-chain or branched ($C_1$–$C_4$) alkanediyl group, preferably a direct bond;

Y and Z are identical or different and independently of one another are in each case $CH_2$, oxygen or a group $S(O)_x$ where x its 0, 1 or 2;

W is a group $(CH_2)_n$ where n is an integer from 1 to 4, or

W, in the event that Y and/or Z are $CH_2$, can be a direct bond between Y and Z; one or more hydrogen atoms in the group —Y—W—Z— being replaced by =U=V=R$^6$ and, if appropriate, by R$^5$, as shown in formula I and described hereinbelow;

a and b are identical or different and independently of one another are the numbers 0, 1, 2 or 3, a and b not simultaneously being 0;

R$^4$ and R$^5$ are identical or different and independently of one another are in each case halogen, alkyl, haloalkyl, alkoxy, haloalkoxy or alkylthio;

r and s are identical or different and independently of one another are 0, 1 or 2;

U is a single bond, oxygen, a group $S(O)_y$ where y is 0, 1 or 2 or a group $NR^7$ where $R^7$ is hydrogen, ($C_1$–$C_4$)-alkyl or ($C_1$–$C_4$)-alkoxy;

V is a single bond, carbonyl or a group of the formula

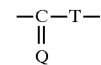

or

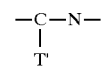

where Q is oxygen, sulfur or ($C_1$–$C_4$)-alkylimino, T is oxygen, sulfur or a group $NR^{7'}$, and T' is ($C_1$–$C_4$)-alkoxy, ($C_1$–$C_4$)-alkylthio or $NR^{7'}R^{7''}$, and where $R^{7'}$ and $R^{7''}$ are identical or different and are as defined above for $R^7$; or U and V together are a double bond; and a) R$^6$ is alkyl, alkenyl, alkynyl, optionally substituted aryl, optionally substituted heterocyclyl or cyano, or, in the event that U and V together are a direct single bond, b) R$^6$ is as defined above or is halogen, hydroxyl, carboxyl, nitro or a group $SiR^8R^9R^{10}$ where $R^8$ and $R^9$ are ($C_1$–$C_4$)-alkyl and $R^{10}$ is alkyl or optionally substituted aryl, or, in the event that U and V together are a double bond, c) R$^6$ is alkylidene or alkyloximino; and the alkyl, alkenyl, alkynyl, alkylidene or alkyloximino radicals mentioned under a), b) or c) for R$^6$, R$^8$, R$^9$ and R$^{10}$ have, if appropriate, at least one of the following characteristics:

i. one or more, preferably up to three, non-adjacent $CH_2$ groups are replaced by CO and/or heteroatom units, such as O, $S(O)_y$ where y is 0, 1 or 2, $NR^{7''}$ or $SiR^{8'}R^{9'}$, where $R^{7''}$ is as defined above for $R^7$ and where $R^{8'}$ and $R^{9'}$ are as defined above for $R^8$ and $R^9$;

ii. 3 to 12 atoms of these radicals form an up to 12-membered cycle;

iii. the hydrocarbon radicals, with or without the above-mentioned variations, are optionally substituted by one or more, preferably up to three, in the case of fluorine up to the maximum number of, identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems among the substituents which have just been mentioned to be unsubstituted or to be provided with up to three, in the case of halogen, preferably fluorine, also up to the maximum number of, identical or different substituents; and furthermore, in the event that $R^5$ and $R^6$ are alkyl radicals, it being possible for these to be linked cyclically or else spirocyclically; and the salts thereof, preferably acid addition salts.

Preferred compounds of the formula I are those in which $R^4$ and $R^5$ are halogen, preferably fluorine, chlorine and bromine, $(C_1-C_4)$-alkyl, $(C_1-C_4)$-haloalkyl, $(C_1-C_4)$-alkoxy, $(C_1-C_4)$-haloalkoxy or $(C_1-C_4)$-alkylthio; and a) $R^6$ is $(C_1-C_{20})$-alkyl, $(C_2-C_{20})$-alkenyl, $(C_2-C_{20})$-alkynyl, optionally substituted aryl, optionally substituted heterocyclyl or cyano, or, in the event that U and V together are a single bond, b) $R^6$ is as defined above or is halogen, hydroxyl, carboxyl, nitro or a group $SiR^8R^9R^{10}$ where $R^8$ and $R^9$ are $(C_1-C_4)$-alkyl and $R^{10}$ is $(C_1-C_{20})$-alkyl or optionally substituted aryl, or in the event that U and V together are a double bond, c) $R^6$ is $(C_1-C_{20})$-alkylidene or $(C_1-C_{20})$-alkyloximino; and the alkyl, alkenyl, alkynyl, alkylidene or alkyloximino radicals mentioned under a), b) or c) for $R^6$, $R^8$, $R^9$ and $R^{10}$ have, if appropriate, at least one of the following characteristics:

i. one or more, preferably up to three, non-adjacent $CH_2$ groups are replaced by CO and/or heteroatom units, such as O, $S(O)_y$ where y is 0, 1 or 2, $NR^{7''}$ or $SiR^{8'}R^{9'}$, where $R^{7''}$ is as defined above for $R^7$ and where $R^{8'}$ and $R^{9'}$ are as defined above for $R^8$ and $R^9$;

ii. 3 to 8 atoms of these radicals form an up to 8-membered cycle;

iii. the hydrocarbon radicals, with or without the above-mentioned variations, are optionally substituted by one or more, preferably up to three, in the case of halogen up to the maximum number of, identical or different radicals selected from the group consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_{12})$-alkanoyl, $(C_3-C_8)$-cycloalkanoyl, $(C_2-C_{12})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to be provided with up to three, in the case of halogen, preferably fluorine, also up to the maximum number of, identical or different substituents, and, in the event that $R^5$ and $R^6$ are alkyl radicals, it furthermore being possible for these to be cyclically or spirocyclically linked, and the remaining radicals and variables are as defined above;

and their salts, preferably acid addition salts.

More preferred compounds of the formula I are those in which $R^1$ is hydrogen, chlorine or fluorine;

$R^2$ is $(C_1-C_4)$-alkyl, $(C_1-C_4)$-haloalkyl, $(C_2-C_4)$-alkenyl, $(C_2-C_4)$-alkynyl, trimethylsilylethynyl, $(C_2-C_4)$-haloalkenyl, cyclopropyl, halocyclopropyl, methoxymethyl or cyano;

$R^3$ is hydrogen, halogen, methyl, ethyl, $(C_2-C_4)$-alkenyl, $(C_2-C_4)$-alkynyl, trimethylsilylethynyl, $(C_2-C_4)$-haloalkenyl, methoxy, ethoxy, cyano or $(C_1-C_4)$-alkoxycarbonyl; or $R^2$ and $R^3$ together with the carbon atoms to which they are bonded form an optionally substituted unsaturated 5- or 6-membered ring which, in the event of a 5-membered ring, can contain a sulfur atom in place of a $CH_2$ unit, or $R^2$ and $R^3$ together with the carbon atoms to which they are bonded form a saturated 5- or 6-membered ring which can contain a sulfur or an oxygen atom in place of a $CH_2$ unit;

A is CH or N;

X is NH or oxygen;

E is a direct bond;

Y and Z are identical or different and are in each case $CH_2$, oxygen or sulfur, and the group —Y—W—Z— is substituted as described above;

a and b are in each case the number 2, $R^4$ and $R^5$ are identical or different and are in each case $(C_1-C_4)$-alkyl, trifluoromethyl or $(C_1-C_4)$-alkoxy;

and the remaining radicals and variables are as defined above;

and their salts;

in particular those compounds in which $R^1$ is hydrogen or fluorine;

$R^2$ is methyl, ethyl, propyl, isopropyl, $(C_1-C_2)$-fluoroalkyl, ethynyl, trimethylsilylethynyl, cyclopropyl or methoxymethyl;

$R^3$ is halogen, methyl, ethyl, ethynyl, trimethylsilylethynyl, methoxy, ethoxy or cyano, or $R^2$ and $R^3$ together with the ring system to which they are bonded form the quinazoline or quinoline system which can be substituted in the carbocyclic moiety by fluorine, or $R^2$ and $R^3$ together with the carbon atoms to which they are bonded form a saturated 6-membered ring which can contain an oxygen or sulfur atom in place of a $CH_2$ group;

Y and Z are identical or different and are in each case $CH_2$ or oxygen and the group —Y—W—Z— is substituted as described above;

r is 0;

$R^5$ is methyl or trifluoromethyl;

U is a direct bond or oxygen;

V is a direct bond; or

U and V together are a double bond; and the remaining radicals and variables are as defined above; and their salts.

Particularly preferred compounds of the formula I are those in which $R^1$ is hydrogen;

$R^2$ is ethyl, propyl, isopropyl, 1-fluoroethyl, ethynyl, trimethylsilylethynyl, trifluoromethyl or methoxymethyl, $R^3$ is fluorine, chlorine, bromine, ethynyl, trimethylsilylethynyl or methoxy; or, in the event that A is nitrogen, $R^2$ and $R^3$ together with the ring system to which they are bonded form the quinazoline system which can be substituted by a fluorine atom, or $R^2$ and $R^3$ together with the ring system to which they are bonded form the 5,6,7,8-tetrahydroquinazoline system;

A is CH or N;

X is NH or oxygen;

E is a direct bond;

Y and Z are identical or different and are in each case $CH_2$ or oxygen;

W is a group $(CH_2)_n$ where n is 2 or 3, or

W, in the event that Y and/or Z are $CH_2$, can be a direct bond between Y and Z; it being possible for one or more hydrogen atoms in the group —Y—W—Z— to be replaced by =U=V=$R^6$ and, if appropriate, by $R^5$, as shown in formula I and described above;

a and b are a and b are the number 2;

r is 0;

s is 0, 1 or 2;

$R^5$ is methyl;

U is a single bond or oxygen,

V is a single bond;
and the remaining radicals are as defined above;
and their salts;

in particular those in which

Y is $CH_2$;

Z is $CH_2$ or oxygen, and, in this case,

W is a direct bond between Y and Z;

or Y and Z are oxygen and, in this case,

W is a group $(CH_2)_n$ and n is a number 2 or 3;

U and V together are a direct single bond;
and the remaining radicals and variables are as defined above;
and their salts.

Most preferred compounds of the formula I are those in which $R^1$ is hydrogen;

$R^2$ is ethyl or methoxymethyl;

$R^3$ is fluorine, chlorine, bromine or methoxy, or $R^2$ and $R^3$ together with the ring system to which they are bonded form the quinazoline or the 5,6,7,8-tetrahydroquinazoline system;

A is CH or N;

X is NH or oxygen;

a and b are in each case 2, and r and s are in each case 0;

E is a direct bond;

Y is $CH_2$ and

Z is $CH_2$ or oxygen,

U and V together are a single bond;
and in this case

W is a direct bond between Y and Z, or Y and Z are in each case oxygen, and in this case W is a group $(CH_2)_n$ which is substituted as described above and n is a number 2 or 3;

—Y—W—Z— is substituted as described; r and s are in each case 0;

$R^6$ is $(C_1-C_{20})$-alkyl, $(C_2-C_{20})$-alkenyl, $(C_2-C_{20})$-alkynyl, optionally substituted aryl or optionally substituted heterocyclyl, and it being possible for one or more, preferably up to two, non-adjacent $CH_2$ groups in the abovementioned alkyl, alkenyl or alkynyl radicals to be replaced by oxygen or sulfur, and, moreover, it being possible for 3 to 6 atoms of these alkyl, alkenyl or alkynyl radicals, with or without the abovementioned variations, to form a cycle, and it being possible for these alkyl, alkenyl or alkynyl radicals, with or without the abovementioned variations including the cyclization, to be optionally substituted by one, in the case of halogen up to the maximum number of, radicals selected from the group consisting of halogen, aryl, aryloxy, arylthio, heterocyclyl, heterocyclyloxy, heterocyclylthio or hydroxyl; and the remaining radicals and variables are as defined above;
in particular those in which $R^2$ is methoxymethyl and $R^3$ is methoxy, or $R^2$ is ethyl and $R^3$ is chlorine or bromine;

X is NH;

A is nitrogen;

Y and Z are oxygen;

W is a group $(CH_2)_n$ which is optionally substituted as described above and n is the number 2;

$R^6$ is $(C_1-C_{20})$-alkyl, aryl or heterocyclyl, all of which are optionally substituted, and it being possible for one or more, preferably up to two, non-adjacent $CH_2$ groups in the abovementioned alkyl radical to be replaced by oxygen or sulfur, and it furthermore being possible for 3 to 6 atoms, with or without the abovementioned substitution, to form a cycle; and the remaining radicals and variables are as defined above;
and their salts.

In the abovementioned formula, "halogen" is to be understood as meaning a fluorine, chlorine, bromine or iodine atom;

the term "$(C_1-C_4)$-alkyl" as meaning an unbranched or branched hydrocarbon radical having 1 to 4 carbon atoms, such as, for example, the methyl, ethyl, propyl, isopropyl, 1-butyl, 2-butyl, 2-methylpropyl or tert-butyl radical;

the term "$(C_1-C_8)$-alkyl" as meaning the abovementioned alkyl radicals, and also, for example, the pentyl, 2-methylbutyl, 1,1-dimethylpropyl, hexyl, heptyl, octyl or the 1,1,3,3-tetramethylbutyl radical;

the term "$(C_1-C_{20})$-alkyl" the abovementioned alkyl radicals and also for example, the nonyl, 1-decyl, 2-decyl, undecyl, dodecyl, pentadecyl or eicosyl radical;

the term "$(C_1-C_4)$-haloalkyl" an alkyl group mentioned under the term "$(C_1-C_4)$-alkyl" in which one or more hydrogen atoms are replaced by the abovementioned halogen atoms, preferably chlorine or fluorine, such as, for example, the trifluoromethyl group, the 1-fluoroethyl group, the 2,2,2-trifluoroethyl group, the chloromethyl group, the fluoromethyl group, the difluoromethyl group or the 1,1,2,2-tetrafluoroethyl group;

the term "$(C_1-C_2)$-fluoroalkyl" for example the mono-, di- and trifluoromethyl group, or the 1-fluoroethyl, 2-fluoroethyl, 1,1-difluoroethyl, 2,2,2-trifluoroethyl or the pentafluoroethyl group;

the term "$(C_1-C_{20})$-alkylidene" for example the exomethylene, ethylidene, propylidene, 1-methylpropylidene, butylidene, octylidene or dodecylidene group, the term "$(C_1-C_{20})$-alkyloximino" an oximino group which is etherified on the oxygen with one of the alkyl groups mentioned the term "$(C_1-C_{20})$-alkyl";

the term "cycloalkyl" preferably $(C_3-C_8)$-cycloalkyl;

the term "cycloalkoxy" preferably $(C_3-C_8)$-cycloalkoxy;

the term "cycloalkylthio" preferably $(C_3-C_8)$-cycloalkylthio;

the term "$(C_3-C_5)$-cycloalkyl" the cyclopropyl, cyclobutyl or cyclopentyl group;

the term "$(C_3-C_8)$-cycloalkyl" the radicals mentioned above under "$(C_3-C_5)$-cycloalkyl" and also the cyclohexyl, cycloheptyl or cyclooctyl radical; but also bicyclic systems such as, for example, the norbornyl or bicyclo[2.2.2]octyl radical;

the term "$(C_3-C_5)$-halocycloalkyl" one of the abovementioned $(C_3-C_5)$-cycloalkyl radicals in which one or more, in the case of fluorine optionally also all, hydrogen atoms are replaced by halogen, preferably fluorine or chlorine, such as, for example, the 2,2-difluoro- or 2,2-dichlorocyclopropane group or the fluorocyclopentane radical;

the term "$(C_2-C_4)$-alkenyl" for example the vinyl, allyl, 2-methyl-2-propenyl or 2-butenyl group;

the term "$(C_2-C_{20})$-alkenyl" the abovementioned radicals and also, for example, the 2-pentenyl, 2-decenyl or 2-eicosenyl group;

the term "$(C_2-C_4)$-haloalkenyl" a $(C_2-C_4)$-alkenyl group in which some of the hydrogen atoms or, in the case of fluorine, also all hydrogen atoms, are replaced by halogen, preferably fluorine or chlorine;

the term "$(C_2-C_4)$-alkynyl" for example the ethynyl, propargyl, 2-methyl-2-propynyl or 2-butynyl group; the term "$(C_2-C_{20})$-alkynyl" the abovementioned radicals and also, for example, the 2-pentynyl or the 2-decynyl group;

the term "$(C_2-C_4)$-haloalkynyl" a $(C_2-C_4)$-alkynyl group in which some of the hydrogen atoms, in the case of fluorine also all hydrogen atoms, are replaced by halogen atoms, preferably fluorine or chlorine; the term "tri-$(C_1-C_4)$-alkylsilyl-$(C_2-C_4)$-alkynyl" preferably the tri-methylsilyl group;

the term "$(C_1-C_4)$-hydroxyalkyl" for example the hydroxymethyl, 1-hydroxyethyl, 2-hydroxyethyl, 1-hydroxy-1-methylethyl or 1-hydroxypropyl group;

the term "$(C_1-C_4)$-alkanoyl" for example the formyl, acetyl, propionyl, 2-methylpropionyl or butyryl group;

the term "$(C_1-C_{12})$-alkanoyl" for example the abovementioned radicals and also, for example, the valeroyl, pivaloyl, hexanoyl, decanoyl or dodecanoyl group;

the term "$(C_2-C_4)$-halalkanoyl" a $(C_1-C_4)$-alkanoyl group in which some of the hydrogen atoms, in the case of fluorine also all hydrogen atoms, are replaced by halogen atoms, preferably fluorine or chlorine;

the term "$(C_2-C_{12})$-haloalkanoyl" a $(C_1-C_{20})$-alkanoyl group in which some of the hydrogen atoms, in the case of fluorine also all hydrogen atoms, are replaced by halogen atoms, preferably fluorine or chlorine;

the term "cyano-$(C_1-C_4)$-alkyl" a cyanoalkyl group whose hydrocarbon radical is as defined under the term "$(C_1-C_4)$-alkyl";

the term "$(C_1-C_4)$-alkoxycarbonyl" for example the methoxycarbonyl, ethoxycarbonyl, propoxycarbonyl, butoxycarbonyl or tert-butoxycarbonyl group;

the term "$(C_1-C_{12})$-alkoxycarbonyl" the abovementioned radicals and also, for example, the hexyloxycarbonyl, 2-methylhexyloxycarbonayl, decyloxycarbonyl or dodecyloxycarbonyl group;

the term "$(C_1-C_4)$-haloalkoxycarbonyl" a $(C_1-C_4)$-alkoxycarbonyl group in which one or more, in the case of fluorine optionally also all, hydrogen atoms, are replaced by halogen, preferably fluorine or chlorine;

the term "$(C_1-C_4)$-alkylthio" an alkylthio group whose hydrocarbon radical is as defined under the term "$(C_1-C_4)$-alkyl";

the term "$(C_1-C_4)$-haloalkylthio" a $(C_1-C_4)$-alkylthio group in which one or more, in the case of fluorine optionally also all, hydrogen atoms of the hydrocarbon moiety are replaced by halogen, in particular chlorine or fluorine;

the term "fluoromethylthio" the mono-, di- and trifluoromethylthio group;

the term "$(C_1-C_4)$-alkylsulfinyl" for example the methyl-, ethyl-, propyl-, isopropyl-, butyl-, isobutyl-, secbutyl- or tert-butylsulfinyl group;

the term "$(C_1-C_4)$-alkylsulfonyl" for example the methyl-, ethyl-, propyl-, isopropyl-, butyl-, isobutyl-, secbutyl- or tert-butylsulfonyl group;

the terms "$(C_1-C_4)$-haloalkylsulfinyl" and "$(C_1-C_4)$-haloalkylsulfonyl" $(C_1-C_4)$-alkylsulfinyl and -sulfonyl radicals as defined above in which one or more, in the case of fluorine optionally also all, hydrogen atoms of the hydrocarbon moiety are replaced by halogen, in particular chlorine or fluorine;

the terms "fluoromethylsulfinyl" and "fluoromethylsulfonyl" the mono-, di- and trifluoromethylsulfinyl and -sulfonyl group;

the term "$(C_1-C_4)$-alkoxy" an alkoxy group whose hydrocarbon radical is as defined under the term "$(C_1-C_4)$-alkyl"; the term "$(C_1-C_4)$-haloalkoxy" a haloalkoxy group whose halohydrocarbon radical is as defined under the term "$(C_1-C_4)$-haloalkyl";

the term "$(C_1-C_4)$-alkoxy-$(C_1-C_4)$-alkyl" for example a 1-methoxyethyl group, a 2-methoxyethyl group, a 2-ethoxyethyl group, a methoxymethyl or ethoxymethyl group, a 3-methoxypropyl group or a 4-butoxybutyl group;

the terms "$(C_1-C_4)$-haloalkoxy-$(C_1-C_4)$-alkyl", "$(C_1-C_4)$-alkoxy-$(C_1-C_4)$-haloalkyl" and "$(C_1-C_4)$-haloalkoxy-$(C_1-C_4)$-haloalkyl" $(C_1-C_4)$-alkoxy-$(C_1-C_4)$-alkyl radicals as defined above in which one or more, in the case of fluorine optionally also all, hydrogen atoms of the relevant hydrocarbon moieties are replaced by halogen, preferably chlorine or fluorine;

the term "($C_1$–$C_4$)-alkylthio-($C_1$–$C_4$)-alkyl" for example methylthiomethyl, ethylthiomethyl, propylthiomethyl, 2-methylthioethyl, 2-ethylthioethyl or 3-methylthiopropyl;

the term "aryl" an isocyclic aromatic radical having preferably 6 to 14, in particular 6 to 12, carbon atoms, such as, for example, phenyl, naphthyl or biphenylyl, preferably phenyl;

the term "heterocyclyl" a heteroaromatic or heteroaliphatic ring system, "heteroaromatic ring system" to be understood as meaning an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

the term "heteroaliphatic ring system" a ($C_3$–$C_8$)-cycloalkyl radical in which at least one carbon unit is replaced by O, S or a group $NR^{11}$ and $R^{11}$ is hydrogen, ($C_1$–$C_4$)-alkyl, ($C_1$–$C_4$)-alkoxy or aryl; the term "arylthio" for example the phenylthio or the 1- or 2-naphthylthio group;

the term "aryloxy" for example the phenoxy or 1- or 2-naphthyloxy group;

the term "heterocyclyloxy" or "heterocyclylthio" one of the abovementioned heterocyclic radicals which are linked via an oxygen or sulfur atom;

the term "($C_3$–$C_8$)-cycloalkoxy" or "($C_3$–$C_8$)-cycloalkylthio" one of the abovementioned ($C_3$–$C_8$)-cycloalkyl radicals which are linked via an oxygen or sulfur atom; the term "aroyl" for example the benzoyl, naphthoyl or biphenylcarbonyl group;

the term "aryl-($C_1$–$C_4$)-alkanoyl" for example the phenylacetyl, 3-phenylpropionyl, 2-phenylpropionyl, 2-methyl-2-phenylpropionyl, 4-phenylbutyryl or naphthylacetyl group;

the term "($C_3$–$C_8$)-cycloalkyl-($C_1$–$C_4$)-alkanoyl" for example the cyclopropylcarbonyl, cyclobutylcarbonyl, cyclopentylcarbonyl, cyclohexycarbonyl, cyclohexylacetyl or cyclohexylbutyryl group;

the term "heterocyclyl-($C_1$–$C_4$)-alkanoyl" for example the thenoyl, furoyl, nicotinoyl, thienylacetyl or pyridinepropionyl group;

the term "($C_3$–$C_8$)-cycloalkoxycarbonyl" for example the cyclobutyloxycarbonyl, cyclopentyloxycarbonyl, cyclohexyloxycarbonyl or cycloheptyloxycarbonyl group; the term "($C_3$–$C_8$)-cycloalkyl-($C_1$–$C_4$)-alkoxycarbonyl" for example the cyclopropylmethoxycarbonyl, cyclobutylmethoxycarbonyl, cyclopentyloxymethoxycarbonyl, cyclohexyloxymethoxycarbonyl, 1-(cyclohexyl)-ethoxycarbonyl or 2-(cyclohexyl)-ethoxycarbonyl group;

the term "aryl-($C_1$–$C_4$)-alkoxycarbonyl" for example the benzyloxycarbonyl, 1-naphthylmethoxycarbonyl, 2-naphthylmethoxycarbonyl, 1-phenyl-ethoxycarbonyl or 2-phenylethoxycarbonyl group; the term "heterocyclyl-($C_1$–$C_4$)-alkoxycarbonyl", for example the thienylmethoxycarbonyl, furylmethoxycarbonyl, tetrahydrofurylmethoxycarbonyl or pyridylethoxycarbonyl group;

the term "aryloxycarbonyl" for example the phenoxycarbonyl, naphthoxycarbonyl or biphenyloxycarbonyl group;

the term "heterocyclyloxycarbonyl" for example the tetrahydropyran-4-oxycarbonyl group;

the term "($C_1$–$C_{20}$)-alkanoyloxy" for example the formyloxy, acetoxy, propionyloxy, butyryloxy, pivaloyloxy, valeroyloxy or hexanoyloxy group;

the term "($C_2$–$C_{20}$)-haloalkanoyloxy" a ($C_2$–$C_{20}$)-alkanoyloxy group in which one or more, in the case of fluorine optionally also all, hydrogen atoms of the hydrocarbon moiety are replaced by halogen, in particular fluorine or chlorine;

the term "($C_3$–$C_8$)-cycloalkanoyloxy" for example the cyclopropanoyloxy, cyclobutenoyloxy, cyclopentanoyloxy, cyclohexanoyloxy or cycloheptanoyloxy group; the term "($C_3$–$C_8$)-cycloalkyl-($C_1$–$C_4$)-alkanoyloxy" for example the cyclopropylcarbonyloxy, cyclopropylacetoxy, cyclobutylcarbonyloxy, cyclopentylcarbonyloxy, cyclohexylcarbonyloxy, cyclohexylacetoxy or 4-cyclohexylbutyryloxy group;

the term "aroyloxyl" for example the benzoyloxy or naphthoyloxy group;

the term "aryl-($C_1C_4$)-alkanoyloxy" for example the benzoyloxy, naphthoyloxy, biphenylcarbonyloxy, phenylacetoxy or phenylbutyryloxy group;

the term "heterocyclyl-($C_1$–$C_4$)-alkanoyloxy" for example the thienylcarbonyloxcy, thienylacetoxy, pyridylcarbonyloxy or pyrimidinylcarbonyloxy group;

the term "($C_1$–$C_{20}$)-alkylsulfonyloxy" for example the methane-, ethane-, butane- or hexanesulfonyloxy group;

the term "arylsulfonyloxy" for example the phenylsulfonyloxy or the toluenesulfonyloxy group.

The substituents with which the various aliphatic, aromatic and heterocyclic ring systems can be provided include, for example, halogen, nitro, cyano, di-($C_1$–$C_4$)-alkylamino, ($C_1$–$C_4$)-alkyl, ($C_3$–$C_8$)-cycloalkyl, ($C_1$–$C_4$)-trialkylsilyl, ($C_1$–$C_4$)-alkoxy, ($C_1$–$C_4$)-alkoxy-($C_1$–$C_4$)-alkyl, ($C_1$–$C_2$)-alkoxy- $[CH_2CH_2O]_{1,2}$-ethoxy, ($C_1$–$C_4$)-alkylthio, ($C_1$–$C_4$)-alkylsulfinyl, ($C_1$–$C_4$)-alkylsulfonyl, thiocyano, ($C_1$–$C_4$)-haloalkyl, ($C_1$–$C_4$)-haloalkoxy, ($C_1$–$C_4$)-haloalkylthio, ($C_2$–$C_4$)-haloalkylsulfinyl, ($C_1$–$C_4$)-haloalkylsulfonyl, ($C_2$–$C_4$)-alkenyl, ($C_2$–$C_4$)-haloalkenyl, trimethylsilylethynyl, ($C_1$–$C_4$)-alkanoyl, ($C_1$–$C_4$)-alkoxycarbonyl, 4-acetylpiperazin-1-yl, phenyl, benzyl, phenoxy, halophenoxy, ($C_1$–$C_4$)-alkylphenoxy, ($C_1$–$C_4$)-alkoxyphenoxy, phenylthio, heterocyclyl, heterocyclylthio or heterocyclyloxy, it being possible for one or more hydrogen atoms, in the case of fluorine also up to the maximum number of hydrogen atoms, in the alkyl radicals and the radicals derived therefrom to be replaced by halogen, preferably chlorine or fluorine, and it being possible, in the event that these substituents are ($C_1$–$C_4$)-alkyl, for these substituents also to be cyclically linked, it being possible for one or two aliphatic carbon units in these condensed ring systems, such as, for example, the indane, di-, tetra- or decahydronaphthyl or benzocycloheptane system, to be replaced by heteroatom units, such as oxygen or sulfur, and it being possible for one or more hydrogen atoms, in the case of fluorine also up to the maximum number of hydrogen atoms, on the aliphatic carbon atom units to be replaced by halogen or ($C_1$–$C_4$)-alkyl.

Furthermore, the definition that "it being possible for one or more, preferably up to three, non-adjacent saturated carbon units in the abovementioned alkyl, alkenyl or alkynyl radicals to be replaced by a carbonyl group or by heteroatoma units, such as oxygen, $S(O)_x$ where x is 0, 1 or 2, $NR^6$ or $SiR^7R^8$, where $R^6$ is hydrogen, ($C_1$–$C_4$)-alkyl, ($C_1$–$C_4$)-alkoxy or ($C_1$–$C_4$)-alkanoyl and $R^7$ and $R^8$ are ($C_1$–$C_4$)-alkyl, preferably methyl, and it furthermore being possible for 3 to 12 atoms of these hydrocarbon radicals which are optionally modified as above to form a cycle and it being possible for these hydrocarbon radicals, with or without the abovementioned variations, to be optionally substituted by one or more, preferably up to three, in the case of fluorine up to the maximum number of, identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanioyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to be provided with up to three, in the case of fluorine also up to the maximum number of, identical or different substituents,", is to be understood as meaning for example:

alkoxyalkyl radicals, such as, for example, the methoxymethyl, methoxyethyl or ethoxyethyl group; or alkoxyalkoxyalkyl radicals, such as, for example, the methoxy- or ethoxyethoxyethyl group; or alkylthioalkyl radicals, such as, for example, the methyl- or ethylthioethyl group; or alkylsulfinylalkyl radicals, such as, for example, the methyl- or ethylsulfinylethyl group; or alkylsulfonylalkyl radicals, such as, for example, the methyl- or ethylsulfonylethyl group; or alkyldialkylsilylalkyl, preferably alkyldimethylsilylalkyl, radicals, such as, for example, the trimethylsilylmethyl or trimethylsilylethyl group; or trialkylsilyl, preferably alkyldimethylsilyl radicals, such as, for example, the trimethylsilyl, ethyldimethylsilyl, tert-butyldimethylsilyl or octyldimethylsilyl group; or cycloalkyldialkylsilyl, preferably cycloalkyldimethylsilyl radicals, such as, for example, the cyclohexyldimethylsilyl group; or aryldialkylsilyl, preferably aryldimethylsilyl radicals, such as, for example, the phenyldimethylsilyl group; or arylalkyldialkylsilyl, preferably aryldimethylsilyl radicals, such as, for example, the benzyldimethylsilyl or phenylethyldimethylsilyl group; or alkanoylalkyl radicals, such as, for example, the acetylmethyl or pivaloylmethyl group; or cycloalkanoylalkyl radicals, such as, for example, the cyclopropylcarbonylmethyl or cyclohexylcarbonylmethyl group; or haloalkanoylalkyl radicals, such as, for example, the trifluoro- or trichloroacetylmethyl group; or aroylalkyl radicals, such as, for example, the benzoyl- or naphthoylalkyl radicals, such as, for example, the phenylacetylmethyl group; or heterocyclylcarbonylalkyl radicals, such as, for example, the thienyl- or pyridylacetylmethyl group; or arylalkyl radicals, such as, for example, the benzyl, 2-phenylethyl, 1-phenylethyl, 1-methyl-1-phenylethyl, 3-phenylpropyl, 4-phenylbutyl, 2-methyl-2-phenylethyl or 1-methyl- or 2-methyl-naphthyl group; or heterocyclylalkyl radicals, such as, for example, the thienylmethyl, pyridylmethyl, furfuryl, tetrahydrofurfuryl, tetrahydropyranylmethyl or 1,3-dioxolane-2-methyl group; or aryloxyalkyl radicals, such as, for example, the phenoxymethyl or naphthoxymethyl group; or cycloalkyl radicals, either monocyclic such as, for example, the cyclopropyl, cyclobutyl, cyclopentyl, cyclohexyl, cycloheptyl or cyclooctyl radical, bicyclic, such as, for example, the norbornyl radical or the bicyclo[2.2.2]octane radical, or condensed, such as the decahydronaphthyl radical;

alkylcycloalkyl radicals, such as, for example, the 4-methyl- or 4-tert-butylcyclohexyl group or the 1-methylcyclopropyl, -cyclobutyl, -cyclopentyl or -cyclohexyl group;

cycloalkylalkyl radicals, such as, for example, the cyclohexylmethyl or -ethyl group; or else haloalkyl derivatives of the corresponding groups, such as, for example, haloalkyl, haloalkoxyalkyl, alkoxyhaloalkyl, haloalkylcycloalkyl or halocycloalkyl radicals.

The illustration above applies analogously to homologs or radicals derived therefrom.

The present invention relates to the compounds of the formula I in the form of the free base or in the form of an acid addition salt. Acids which can be used for the formation of salts are inorganic acids, such as hydrochloric acid, hydrobromic acid, nitric acid, sulfuric acid, phosphoric acid, or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Some of the compounds of the formula I have one or more asymmetric carbon atoms or stereoisomers on double bonds. Enantiomers or diaestereomers may therefore occur. The invention embraces the pure isomers and also their mixtures. The mixtures of diastereomers can be separated into the components by customary methods, for example by selective crystallization from suitable solvents or by chromatography. Racemates can be resolved into the enantiomers by customary methods, for example by salt formation using an optically active acid, separation of the diastereomeric salts and liberation of the pure enantiomers by means of a base.

The invention furthermore relates to a process for the preparation of compounds of the formula I which comprises reacting a compound of the formula II

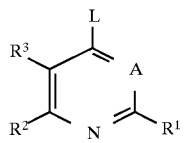
(II)

in which A, $R^1$, $R^2$ and $R^3$ are as defined under formula I and L is a leaving group such as, for example, halogen, alkylthio, alkanesulfonyloxy or arylsulfonyloxy, alkylsulfonyl or arylsulfonyl, with a nucleophile of the formula III

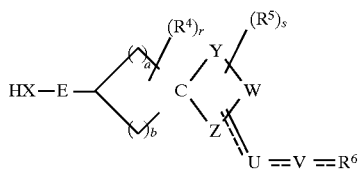
(III)

in which a, b, r, s, E, U, V, W, X, Y, Z, $R^4$, $R^5$ and $R^6$ are as defined above under formula I, and optionally subjecting the compounds of the formula I which have been obtained in this or a different manner to further derivatization on the heterocycle and/or in the side chain $R^6$ and, if appropriate, converting the compounds into their salts.

The above-described substitution reaction is known in principle. The leaving group Z can be varied within a wide range and can be, for example, a halogen atom, such as fluorine, chlorine, bromine or iodine; or alkylthio, such as methylthio or ethylthio; or alkanesulfonyloxy, such as methane-, trifluoromethane- or ethanesulfonyloxy; or arylsulfonyloxy, such as benzenesulfonyloxy; or toluenesulfonyloxy, or alkylsulfonyl, such as methyl- or ethylsulfonyl; or arylsulfonyl, such as phenyl- or toluenesulfonyl.

The abovementioned reaction is carried out in a temperature range of 20°–150° C., expediently in the presence of a base and, if appropriate, in an inert organic solvent, such as N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

In the event that X is oxygen or $S(O)_x$, examples of suitable bases are the carbonates, hydrogen carbonates, amides or hydrides of alkali metals or alkaline earth metals, such as sodium carbonate, sodium hydrogen carbonate, potassium carbonate, sodium amide or sodium hydride, in the event that X is NH, suitable bases are, for example, the carbonates, hydrogen carbonates, hydroxides, amides or hydrides of alkali metals or alkaline earth metals, such as sodium carbonate, sodium hydrogen carbonate, potassium carbonate, sodium hydroxide, sodium amide or sodium hydride, or organic bases, such as triethylamine or pyridine, or else a second equivalent of the nucleophile where X=NH.

The invention furthermore relates to a process for the preparation of compounds of the formula I in which Y and Z are oxygen and W is a group $(CH_2)_n$ in which n is 2, 3 or 4, which comprises reacting, in the presence of an acidic catalyst, a compound of the formula IV

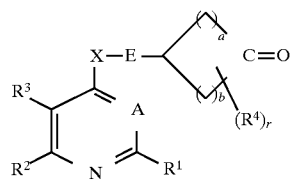
(IV)

in which a, b, r, A, X, E, $R^1$, $R^2$, $R^3$ and $R^4$ are as defined above for formula I, with a diol of the formula V

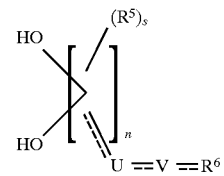
(V)

in which U, V, $R^5$, $R^6$ and s are as defined above and n is a number 2, 3 or 4, to give, with the elimination of water, the compounds of the formula I and, if appropriate, subjecting these compounds to further derivatization in the side chain $R^6$.

The above-described ketalization reaction is known in principle. It is carried out in a temperature range of 20°–200°, preferably between 60° and 150° in the presence of an acidic dehydration catalyst, in substance or in an inert solvent. Examples of suitable catalysts are hydrochloric acid, sulfuric acid, phosphoric acid, sodium hydrogen sulfate, sulfonic acid, such as methane- or toluenesulfonic acid, phosphorus (V) oxide, iron (III) chloride, zinc chloride, anhydrous copper sulfate, iodine or else acidic ion exchangers, such as, for example, ®Amberlite IR-120. The water formed during the reaction is expediently removed by distillation, if appropriate under reduced pressure, or by azeotropic distillation using an entrainer. Examples of suitable entrainers are benzene, toluene, xylene or petroleum ether.

The invention furthermore relates to a process for the preparation of compounds of the formula I in which Y and Z are oxygen and W is a group $(CH_2)_n$ in which n is 2, 3 or 4, which comprises reacting, in the presence of an acidic catalyst, a compound of the formula I'

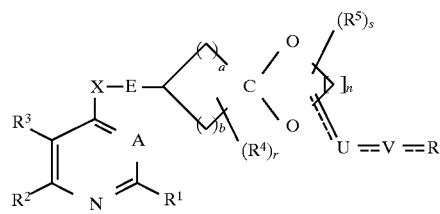
(I')

in which $R^1$, $R^2$, $R^3$, $R^4$, $R^5$, $R^6$, a, b, r, s, A, X and E are as defined for formula I, n is 2, 3 or 4 and s is 0, with a diol of the formula V, to obtain the end products with ketal exchange. The reaction temperature, the solvent and the catalysts correspond to those which have been described in the reaction of the compounds of the formula IV with the compounds of the formula V. The diol V is expediently employed in an excess.

In the event that X is oxygen, the nucleophiles of the formula III, which are required as starting materials, can be prepared by known processes, for example by reducing a carbonyl group with a suitable reducing agent, such as a complex metal hydride, or, in the case of an aldehyde or ketone, also using, for example, hydrogen and a hydrogenation catalyst. Other possibilities are the reaction of an organometallic compound with a carbonyl group or with an oxirane.

In the event that X is NH, the nucleophiles of the formula III, which are required as starting materials, can be prepared by known methods, for example by reducing an oxime or a nitrile with a suitable reducing agent, for example a complex metal hydride or hydrogen in the presence of a hydrogenation catalyst, reductive amination or Leuckart-Wallach reaction of an aldehyde or ketone, or Gabriel reaction of an alkyl halide or alkyl tosylate.

Those nucleophiles of the formula III which are used as precursors for the preferred compounds of the formula I in which E is a direct bond are obtained from the corresponding cycloalkanones of the formula VI

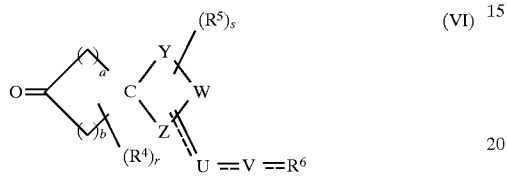

in which a, b, r, s, U, V, W, Y, Z, $R^4$, $R^5$ and $R^6$ are as defined above for formula I, as described above, for example by means of reductive amination or reduction with a complex hydride.

Depending on a, b, r, s, W, Y and Z, these compounds of the formula VI can be prepared by reactions known in principle.

For example, Spiro derivatives of cyclohexanone (a=b=2) can be obtained by the following methods:

a) Y=Z=CH$_2$; W=direct bond (cyclopropane derivatives)

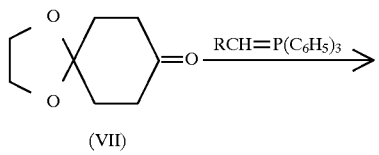

(VII)

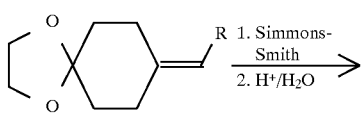

(VIII)

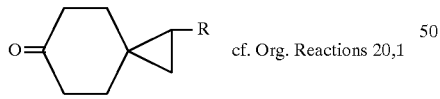

cf. Org. Reactions 20,1

R (here and hereinbelow)=organic radical b) Y=Z=CH$_2$ (cyclobutane derivatives)

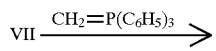

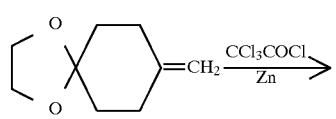

(IX)

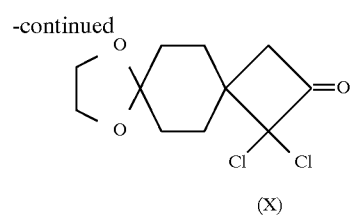

(X)

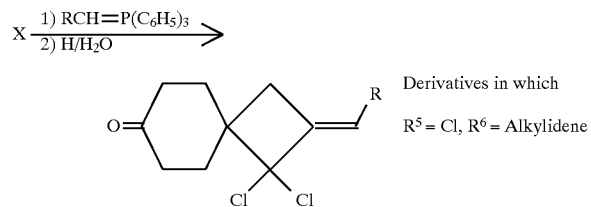

Derivatives in which $R^5$ = Cl, $R^6$ = Alkylidene

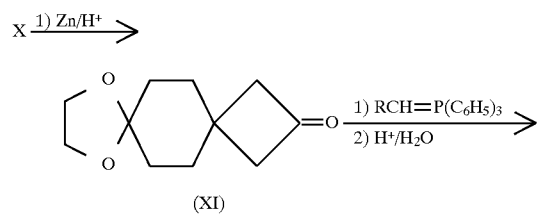

(XI)

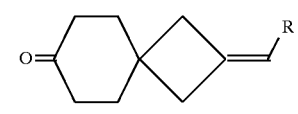

Derivatives in which $R^6$ = Alkylidene

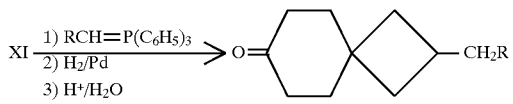

cf. Bull. Soc. Chim. Fr. 1984, 65.

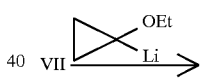

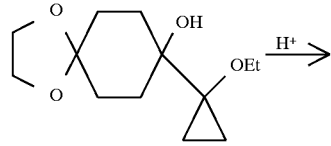

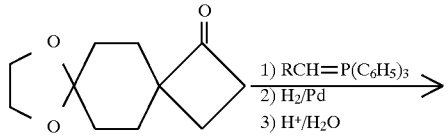

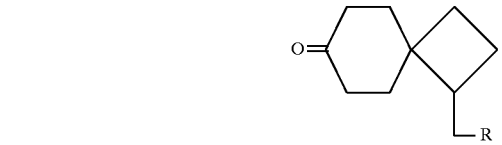

J. Org. Chem. 50 (1985), 3255 c) Y=O, Z=CH$_2$; W=CH$_2$ (oxetane derivatives)

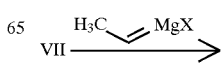

-continued

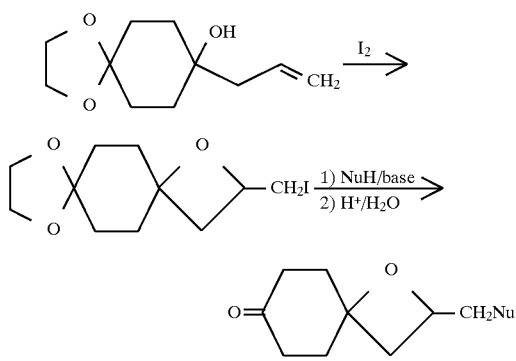

Nu e.g.=HOR, HSR R=alkyl, aryl, etc. Synthesis 1988, 862

3) Y=Z=CH$_2$; W=(CH$_2$)$_n$ (spiroalkanes)

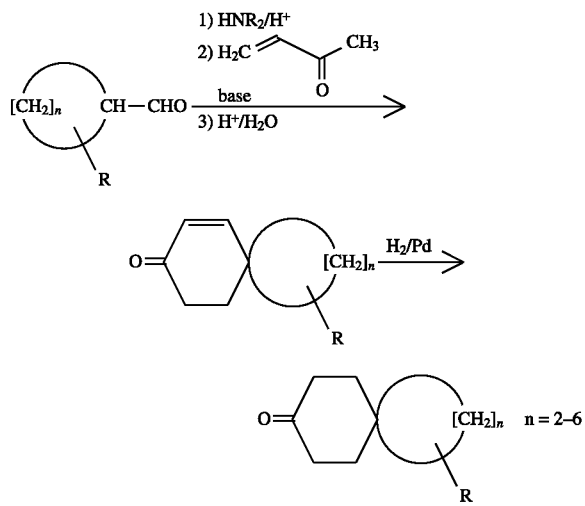

cf. Org. Synth., Coll. Vol. VI, 496 e) Y=CH$_2$; Z=O; W=(CH$_2$)$_n$ (oxa-spiroalkanes)

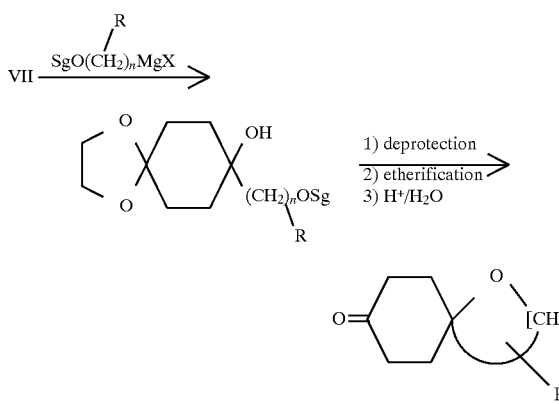

n = 3, 4, 5
Sg = protective group
cf. U.S. Pat. No. 44 38 130 f) Y=Z=O; W=(CH$_2$)$_n$; (ketals)

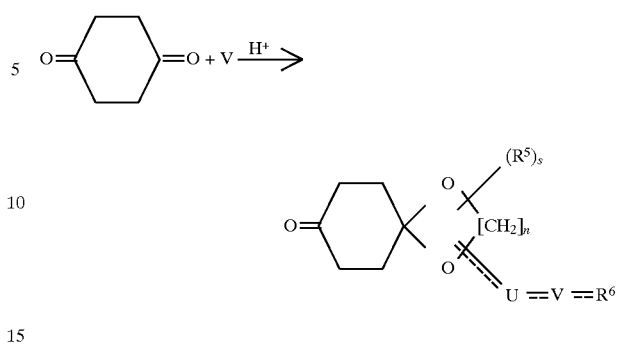

The reactions described under a), b), c) and e) can also be carried out using cyclohexane-1,4-dione as the precursor, albeit with poorer yields.

Suitable precursor which have rings of different sizes (a, b≠2) have also been described (Tetrahedron Lett. 28 (1987) 551).

All reactions starting from cyclohexane-1,4-dione monoketal (VII) can also be carried out with the 4-ketocyclohexylamine derivative IV'.

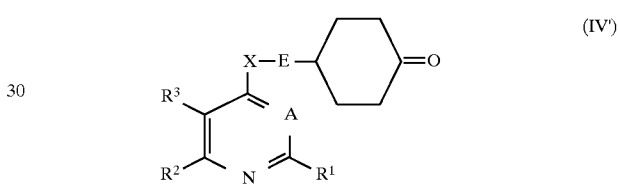

Epoxide derivatives (X=CH$_2$, Z=O, W=direct bond between Y and Z) are best prepared from the ketones IV or the exo-alkylene derivatives XII.

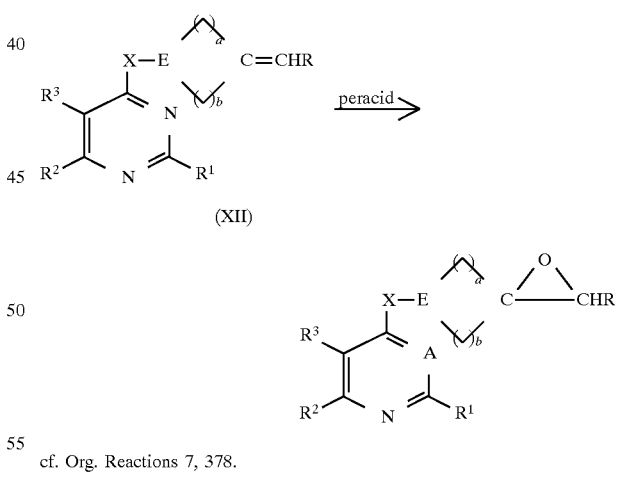

cf. Org. Reactions 7, 378.

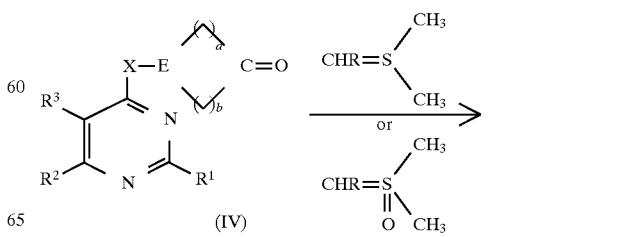

-continued

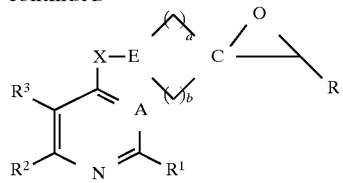

cf. J. Amer. Chem. Soc. 87 (1965) 1353.

The preparation of the precursors of the formulae IV and XII is described in DE-A-43 31 179.

The active substances are suitable for controlling animal pests, in particular insects, arachnids, helminths and mollusks, very particularly preferably for controlling insects and arachnids, encountered in agriculture, in livestock breeding, in forestry, in the protection of stored products and of materials, and in the hygiene field, are well tolerated by plants and have favorable toxicity to warm-blooded species. They are active against normally sensitive and resistant species and against all or some stages of development. The abovementioned pests include:

From the order of the Acarina, for example, *Acarus siro,* Argas spp., Ornithoioros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp., Eutetranychus spp.

From the order of the Isopoda, for example, *Oniscus asellus, Armadillidium vulgare* and *Porcellio scaber.* From the order of the Diplopoda, for example, *Blaniulus guttulatus.*

From the order of the Chilopoda, for example, *Geophilus carpophagus* and Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Isoptera, for example, Reticulitermes spp.

From the order of the Anoplura, for example, *Phylloxera vastatrix,* Pemphigus spp., *Pediculus humanus* corporis, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulanal,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristonreura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the class of the Helminthes, for example, Haemonchus, Trichostrongulus, Ostertagia, Cooperia, Chabertia, Strongyloides, OesophaLgostomum, Hyostrongulus, Ancylostoma, Ascaris and Heterakis, and also Fasciola and plant-pathogenic nematodes, for example those of the genera Meloidogyne, Heterodera, Ditylenchus, Aphelenchoides, Radopholus, Globodera, Pratylenchus, Longidorus and Xiphinema.

From the class of the Gastropoda, for example, Deroceras spp., Arion spp., Lymnaea spp., Galba spp., Succinea spp., Biomphalaria spp., Bulinus spp. and Oncomelania spp.

From the class of the Bivalva, for example, Dreissena spp.

The plant-parasitic nematodes which can be controlled according to the invention include, for example, the root-parasitic soil nematodes, such as, for example, those of the genera Meloidogyne (root knot eel worms, such as *Meloidogyne incognita, Meloidogyne hapla* and *Meloidogyne javanica*), Heterodera and Globodera (cyst nematodes, such as *Globodera rostochiensis, Globodera pallida, Heterodera schachtii, Heterodera avenae, Heterodera glycines* and *Heterodera trifolii*) and of the genera Radopholus, such as *Radopholus similis,* Pratylenchus, such as *Pratylenchus neglectus, Pratylenchus penetrans* and *Pratylenchus curvitatus*; Tylenchulus, such as *Tylenchulus semipenetrans,* Tylenchorhynchus, such as *Tylenchorhynchus dubius* and *Tylenchorhynchus claytoni,* Rotylenchus, such as *Rotylen-*

*chus robustus*, Helicotylenchus, such as *Helicotylenchus multicinctus*, Belonoaimus, such as *Belonoaimus longicaudlatus*, Longidorus, such as *Longidorus elongatus*, Trichodorus, such as *Trichodorus primitivus* and Xiphinema, such as *Xiphinema index*.

Furthermore, the compounds according to the invention can be used to control the nematode genera Ditylenchus (stem parasites, such as *Ditylenchus dipsaci* and *Ditylenchus destructor*), Aphelenchoides (leaf nematodes, such as *Aphelenchoides ritzemabosi*) and Anguina (leaf-gall nematodes, such as *Anguina tritici*).

The invention also relates to compositions, in particular insecticidal, nematocidal and acaricidal compositions, which comprise the compounds of the formula I as well as suitable formulation auxiliaries.

The active substances of the formulae I generally amount to 1 to 95% by weight of the compositions according to the invention.

They can be formulated in various ways, depending on the biological and/or chemico-physical parameters. Possible formulations which are suitable are therefore: wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulations are known in principle and are described, for example, in: Winnacker-Küchler, "Chemische Technologie" [Chemical Technology], Volume 7, C. Hauser Verlag Munich, 4th Ed. 1986; van Falkenberg, "Pesticides Formulations", Marcel Dekker N.Y., 2nd Ed. 1972–73; K. Martens, "Spray Drying Handbook", 3rd Ed. 1979; G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1967; Winnacker-Küchler, "Chemische Technologie", Volume 7, C. Hauser Verlag Munich, 4th Ed. 1986.

Based on these formulations, it is also possible to prepare combinations with other pesticidally active substances, fertilizers and/or growth regulators, for example in the form of a readymix or a tank mix. Wettable powders are preparations which are uniformly dispersible in water and which, besides the active substance, also comprise wetting agents, for example polyoxyethylated alkylphenols, polyoxyethylated fatty alcohols, alkyl sulfonates or alkylphaenol sulfonates, and dispersants, for example sodium lignosulfonate or sodium 2,2'-dinaphthylmethane-6,6'-disulfonate, in addition to a diluent or inert substance.

Emulsifiable concentrates are prepared by dissolving the active substance in an organic solvent, for example butanol, cyclohexanone, dimethylformamide, xylene or else higher-boiling aromatics or hydrocarbons, with the addition of one or more emulsifiers. Examples of emulsifiers which can be used are: calcium alkylarylsulfonates, such as calcium dodlecylbenzenesulfonate, or non-ionic emulsifiers, such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays, such as kaolin, bentonite or pyrophyllite, or diatomaceous earth. Granules can be prepared either by spraying the active substance onto adsorptive granulated inert material or by applying concentrates of active substance to the surface of carriers such as sand, kaolinites or granulated inert material with the aid of binders, for example polyvinyl alcohol, sodium polyacrylate or else mineral oils. Suitable active substances may also be granulated in the manner which is customary for the preparation of fertilizer granules, if desired in the form of a mixture with fertilizers.

The concentration of active substance in wettable powders is, for example, approximately 10 to 90% by weight, the remainder to 100% by weight being composed of customary formulation components. In the case of emulsifiable concentrates, the concentration of active substance may amount to approximately 5 to 80% by weight. Formulations in the form of dusts comprise in most cases 5 to 20% by weight of active substance, sprayable solutions approximately 2 to 20% by weight. In the case of granules, the active substance content depends partly on whether the active compound is in liquid or solid form and on which granulation auxiliaries, fillers etc. are being used.

In addition, the abovementioned formulations of active substances comprise, if appropriate, the adhesives, wetting agents, dispersants, emulsifiers, penetrants, solvents, fillers or carriers which are customary in each case.

For use, the concentrates, which are in commercially available form, are, if appropriate, diluted in the customary manner, for example using water in the case of wettable powders, emulsifiable concentrates, dispersions and some microgranules. Preparations in the form of dusts or granules and sprayable solutions are conventionally not diluted any further with other inert substances before being used.

The application rate required varies with the external conditions, such as, inter alia, temperature and humidity. It can vary within wide limits, for example between 0.0005 and 10.0 kg/ha or more of active substance, but it is preferably between 0.001 and 5 kg/ha.

The active substances according to the invention may be present in the commercially available formulations and in the use forms prepared with these formulations in the form of mixtures with other active substances, such as insecticides, attractants, sterilants, acaricides, nematicides, fungicides, growth-regulating substances or herbicides.

The pesticides include, for example, phosphoric esters, carbamates, carboxylic esters, formamidines, tin compounds, substances prepared by microorganisms and the like. Preferred components in mixtures are:

1. from the group comprising the phosphorus compounds acephate, azamethiphos, azinphos-ethyl, azinphosmethyl, bromophos, bromophos-ethyl, chlorfenvinphos, chlormephos, chlorpyrifos, chlorpyrifos-methyl, demeton, demeton-S-methyl, demeton-S-methylsulfone, dialifos, diazinon, dichlorvos, dicrotophos, O,O-1,2,2,2-tetrachloroethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, pirimiphos-ethyl, pirimiphos-methyl, profenofos, propaphos, propetamphos, prothiofos, pyridaphenthion, quinalphos, sulprofos, temephos, terbufos, tetrachlorvinphos, thiometon, triazophos, trichlorphlon, vamidothion;

2. from the group comprising the carbamates aldicarb, 2-sec-butylphenyl methylcarbamate (BPMC), carbaryl, carbofuran, carbosulfan, cloethocarb, ethiofencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio) carbamate (UC 51717);

3. from the group comprising the carboxylates allethrin, alphametrin, 5-benzyl-3-furylmethyl (E)-(1R) cis-2,2-dimethyl-3-(2-oxothiolan-3-ylidenemethyl) cyclopropanecarboxylate, bioallethrin, bioallethrin ((S) cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, phenothrin (R isomer), d-pralethrin, pyrethrins (natural products), resmethrin, tefluthrin, tetramethrin, tralomethrin;

4. from the group comprising the amidines amitraz, chlordimeform;

5. from the group comprising the tin compounds cyhexatin, fenbutatin oxide;

6. others abamectin, *Bacillus thuringiensis*, bensultap, binapacryl, bromopropylate, buprofezin, camphechlor, cartap, chlorobenzilate, chlorfluazuron, 2-(4-chlorophenyl)-4,5-diphenylthiophene (UBI-T 930), chlorfentezine, 2-naphthylmethyl cyclopropanecarboxylate (Ro12-0470), cyromazin, ethyl N-(3,5-dichloro-4-(1,1,2,3,3,3-hexafluoro-1-propyloxy) phenyl)carbamoyl)-2-chlorobenzocarboximidate, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl) (dimethyl) (3-(3-phenoxyphenyl) propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitrornethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The active substance content of the use forms prepared from the commerically available formulations can range from 0.00000001 to 95% by weight of active substance and is preferably between 0.00001 and 1% by weight.

They are applied in a conventional manner adapted to suit the use forms.

The active substances according to the invention are also suitable for controlling endo- and ectoparasites in the field of veterinary medicine or the field of animal husbandry.

The active substances according to the invention are administered in a known manner, for example by oral administration in the form of, for example, tablets, capsules, potions or granules, by dermal administration, for example in the form of dipping, spraying, pouring-on and spotting on and dusting, and by parenteral administration, for example in the form of injection.

Accordingly, the novel compounds of the formula I according to the invention can also be applied particularly advantageously in livestock husbandry (for example cattle, sheep, pigs and poultry such as chickens, geese and the like). In a preferred embodiment of the invention, the novel compounds, if appropriate in suitable formulations (cf. above) are administered orally to the animals, if appropriate together with the drinking water or the feed. Since the compounds are excreted effectively with the feces, the development of insects in the feces of the animals can be prevented very simply. The dosages and formulations which are suitable in each case depend, in particular, on the species and development stage of the livestock and also on the risk of infection and can readily be determined and fixed by customary methods. In the case of cattle, for example, the novel compounds can be employed in dosages of 0.01 to 1 mg/kg of body weight.

The compounds of the formula I according to the invention are also distinguished by an outstanding fungicidal activity. Fungal pathogens which have already penetrated the plant tissue can successively be controlled curatively. This is particularly important and advantageous in the case of those fungal diseases which can no longer be controlled effectively with the other customary fungicides when infection has taken place already. The spectrum of action of the claimed compounds embraces various economically important phytopathogenic fungi such as, for example, *Plasmopara viticola, Erysiphe graminis* and *Puccinia recondita*.

In addition, the compounds according to the invention are also suitable for use in technical fields, for example as wood preservatives, as preservatives in paints, in cooling lubricants for metalworking, or as preservatives in drilling and cutting oils.

The active substances according to the invention in their commercially available formulations can either be employed on their own or in combination with other fungicides known from the literature.

Examples of fungicides which are known from the literature and which can be combined according to the invention with the compounds of the formula I are the following products:

aldimorph, andoprim, anilazine, BAS 480F, BAS 450F, benalaxyl, benodanil, benomyl, binapacryl, bitertanol, bromuconazole, buthiobate, captafol, captan, carbendazim, carboxin, CGA 1735106, cyprofuram, dichlofluanid, dichlomezin, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazol, fenarimol, fenfuram, fenpiclonil, fenpropiclin, fenpropimorph, fentin acetate, fentin hydroxide, ferinzone (TF164), fluazinam, fluobenzimine, fluquinconazole, fluorimide, flusilazole, flutolanil, flutriafol, folpet, fosetyl-aluminium, fuberidazole, fulsulfamide (MT-F 651), furalaxyl, furconazol, furmecyclox, guazatine, hexaconazole, ICI A5504, imazalil, imibenconazole, iprobenfos, iprodione, isoprothiolane, KNF 317, copper compounds, such as copper oxychloride, oxine-copper, copper oxide, mancozeb, maneb, mepanipyrim (KIF 3535), metconazole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiofanate-methyl, thiram, toldlofos-methyl, tolylfluanid, triadimefon, triadimenol, tricyclazole, tridemorph, triflumizol, triforine, validamycin, vinchlozolin, XRD 563, zineb, sodium dodecylsulfonate, sodium dodecyl sulfate, sodium C13/C15-alcohol ether sulfonate, sodium cetostearyl phosphate ester, sodium dioctylsulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkyl-imidazoline.

The abovementioned components for combinations are known active substances, many of which are described in Ch.R Worthing, S. B. Walker, The Pesticide Manual, 7th Edition (1983), British Crop Protection Council. The active substance content of the use forms prepared from the commercially available formulations can vary within wide limits, and the concentration of active substance in the use forms can range from 0.0001 to 95% by weight of active substance and is preferably between 0.0001 and 1% by weight. They are applied in a customary manner adapted to suit the use forms.

The examples which follow are intended to illustrate the invention without imposing any limitation thereon.

A. FORMULATION EXAMPLES a) A dust is obtained by mixing 10 parts by weight of active substance and 90 parts by weight of talc as inert material and comminuting the mixture in a hammer mill.

b) A wettable powder which is readily dispersible in water is obtained by mixing 25 parts by weight of active substance, 65 parts by weight of kaolin-containing quartz as inert material, 10 parts by weight of potassium lignosulfonate and 1 part by weight of oleoylmethyltaurate as wetting agent and dispersant and grinding the mixture in a pinned-disc mill.

c) A dispersion concentration which is readily dispersible in water is prepared by mixing 40 parts by weight of active substance with 7 parts by weight of a sulfosuccinic monoester, 2 parts by weight of a sodium lignosulfonate and 51 parts by weight of water and grinding the mixture in a ball mill to a fineness of below 5 microns.

d) An emulsifiable concentrate can be prepared from 15 parts by weight of active substance, 75 parts by weight of cyclohexane as the solvent and 10 parts by weight of oxyethylated nonylphenol (10 EO) as the emulsifier.

e) Granules can be prepared from 2 to 15 parts by weight of active substance and an inert granule carrier, such as attapulgite, pumice granules and/or quartz sand. It is expedient to use a suspension of the wettable powder of Example b) with a solids content of 30% which is sprayed onto the surface of attapulgite granules and these are then dried and mixed intimately. The amount of the wettable powder amounts to approximately 5% by weight and the inert carrier to approximately 95% by weight of the finished granules.

B. BIOLOGICAL EXAMPLES

Fungicidal Action

Example 1

*Puccinia recondita*

Wheat cv. "Jubilar" in the 2-leaf stage is treated to runoff point with aqueous suspensions of the claimed compounds.

After the spray coating has dried on, plants are inoculated with an aqueous spore suspension of *Puccinia recondita*. The dripping wet plants are placed in a controlled-environment cabinet at 20° C. and a relative atmospheric humidity of approximately 100% for approximately 15 hours. They are subsequently grown on in a greenhouse at a temperature of 22°–25° C. and a relative atmospheric humidity of 50–70%.

After an incubation time of approximately 2 weeks, the fungus sporulates on the entire leaf surface area of the untreated control plants (100% infection), so that the disease level of the test plants can be evaluated. The disease level is expressed in % diseased leaf area in comparison to the untreated, infected control plants.

At a rate of 500 mg/l of spray mixture, disease is suppressed completely by the following Example numbers: 503, 530, 539, 546, 803, 804, 815, 853.

Acaricidal and Insecticidal Action

Example 2

Bean plants (*Phaseolus vulgaris* ssp. vulgaris var. nanus) which were severely infested with greenhouse red spider mites (*Tetranychus urticae*, full population) were sprayed to beginning runoff point with an aqueous preparation comprising 250 ppm of the active substance in question. After the plants had been grown in the greenhouse for 7 days, the mortality of the spider mites (full population) was checked. A mortality of 100% was found in the case of the following Example numbers: 359, 360, 361, 362, 382, 387, 388, 391, 392, 399, 405, 412, 416, 424, 431, 138, 502, 503, 530, 538, 537, 539, 540, 544, 545, 546, 549, 803, 804, 806, 807, 809, 811, 812, 813, 814, 815, 817, 818, 822, 841, 843, 853, 855, 1049, 1050, 1069.

Example 3

Fruit tree red spider mite

Apple plants (*Malus domestica*) which were severely infested with fruit tree red spider mites (*Panonychus ulmi*, full population) were sprayed to beginning runoff point with an aqueous preparation comprising 250 ppm of the active substance in question. After the plants had been grown in the greenhouse for 9 days, the mortality of the spider mites (full population) was checked. A mortality of 100% was found in the case of the following Example numbers: 278, 359, 360, 361, 362, 382, 388, 391, 392, 399, 405, 412, 416, 431, 438, 502, 503, 530, 536, 537, 538, 539, 540, 544, 545, 546, 549, 803, 804, 806, 807, 809, 811, 812, 813, 814, 815, 817, 818, 819, 822, 824, 825, 841, 843, 853, 855, 1049, 1050, 1066, 1069.

Example 4
Black bean aphid

Field bean plants (*Vicia faba*) which were severely infested with black bean aphids (*Aphis fabae*, full population) were sprayed to beginning runoff point with an aqueous preparation comprising 250 ppm of the active substance in question,, After the plants had been grown in the greenhouse for 3 days, the mortality of the aphids (full population) was checked. A mortality of 100% was found in the case of the following Example numbers: 267, 359, 360, 361, 362, 382, 388, 392, 399, 405, 412, 416, 424, 431, 438, 503, 530, 536, 537, 538, 539, 545, 546, 549, 803, 804, 807, 809, 811, 812, 813, 815, 817, 818, 819, 824, 841, 843, 853, 855, 1049, 1066.

Example 5
Large milkweed bug (eggs)

Filter paper disks supporting eggs (egg age: 2 days) of the large milkweed bug (*Oncopeltus fasciatus*) were treated with in each case 1 ml of an aqueous preparation comprising 250 ppm of the active substance in question. After the coating has dried on, the filter paper disks were stored in Petri dishes at room temperature and maximum atmospheric humidity. After 7 days, the ovicidal action was determined. An ovicidal action (egg mortality) 100% was found in the following Example numbers: 359, 360, 361, 362, 3832, 392, 399, 405, 412, 416, 424, 438, 530, 533, 536, 537, 538, 539, 545, 546, 549, 803, 804, 806, 807, 809, 811, 812, 813, 814, 815, 817, 818, 819, 824, 841, 843, 853, 1049, 1064, 1066, 1069.

Example 6
Action against whitefly

Bean plants (*Phaseolus vulgaris* ssp. vulgaris var. nanus) which were severely infested with whiteflies (*Trialeurodes vaporariorum*, 3-day old eggs) were sprayed to beginning runoff point with an aqueous preparation comprising 250 ppm of the active substance in question. After the plants had been grown in the greenhouse for 14 days, the mortality of the whiteflies (full population) was checked. A mortality of 100% was found in the following Example numbers: 382, 399, 412, 424, 431, 438, 503, 530, 536, 539, 545, 546, 549, 803, 804, 809, 812, 813, 815, 819, 841, 842, 853, 855, 1066.

Example 7
Common citrus mealy bug

Bean plants (*Phaseolus vulgaris* ssp. vulgaris var. nanus) which were severely infested with common citrus mealy bugs (*Planococcus citri*, 2nd instar larvae) were sprayed to beginning runoff point with an aqueous preparation comprising 250 ppm of the active substance in question. After the plants had been grown in the greenhouse for 7 days, the mortality of the common citrus mealy bugs (full population) was checked. A mortality of 100% was found in the following Example numbers: 359, 360, 362, 382, 392, 399, 412, 424, 438, 530, 536, 537, 538, 539, 546, 549, 803, 804, 807, 809, 811, 812, 813, 815, 817, 818, 819, 824, 843, 853, 855, 1049.

Example 8
Root systemic action against the greenhouse red spider mite

An aqueous preparation of the active substance in question was distributed uniformly in the root zone of potted field bean plants (*Vicia faba*) whose root balls were covered by a film (concentration of active substance 25 ppm based on the soil volume). After two days, the plants were infested with greenhouse red spider mites (*Tetranychus urticae*, full population). After the plants had been grown in the greenhouse for a further 7 days, the mortality of the spider mites (full population) was checked. A mortality of 100% was found in the case of the following Example numbers: 360, 399, 804, 807, 813.

Example 9
Stem-systemic action against the greenhouse red spider mite

Three stems of field bean plants (*Vicia faba*) which were severely infested by the greenhouse red spider mite (*Tetranychus urticae*, full population) were provided with a cotton bandage 300 mg in weight. This bandage was treated with 2 ml of an aqueous preparation comprising 500 ppm of the active substance in question. After the treated plants had been grown in the greenhouse for 7 days, the mortality of the spider mites (full population) on the leaves were checked. A mortality of 100% was found in the case of the following Example number: 813.

Example 10
Cockroach (*Blaberus craniifer*)

Larvae (L4) of the cockroach, *Blaberus craniifer*, were injected with active substances dissolved in methanol. A mortality of 100% was found in the case of the following Example numbers: 382, 431, 438, 536, 546, 803, 804, 813, 819, 841, 843, 855.

Example 11

Larvae (L4) of the tobacco hornworm, *Manduca sexta*, were injected with active substances dissolved in acetone. A mortality of 100% was found in the case of the following Example numbers: 382, 431, 438, 536, 546, 803, 804, 813, 819, 841, 843.

Example 12
Common housefly

The bottom and lid of Petri dishes were coated on the inside with in each case 3 ml of an aqueous dilution of a wettable powder concentrate comprising 250 ppm of the active substance in question.

After the coating had dried on, 24-h old common houseflies (*Musca domestica*) were introduced into the Petri dishes, which were sealed with the treated lid. After 3 hours at room temperature (20° C.), the mortality of the flies was checked. A mortality of 100% was found in the case of the following Example numbers: 359, 360, 361, 362, 382, 392, 399, 405, 412, 416, 424, 438, 530, 536, 539, 546, 549, 803, 813, 815, 819, 841.

Example 13
*Diabrotica undecimpunctata*

Filter paper disks were treated with in each case 1 ml of the aqueous dilution of a wettable powder concentrate comprising 250 ppm of the active substance in question and stored in the open until dry. The filter paper was then placed in the bottom of a Petri dish and in each case 1 ml of (distilled) water was added dropwise. 10 larvae (L3) of *Diabrotica undecimpunctata* were subsequently placed on the filter paper, and the Petri dish was sealed and stored at 28° C. in the dark for 48 h. The mortality of the larvae was then determined. A destruction of 100% was found in the case of the following Example numbers: 267, 359, 360, 382, 388, 392, 412, 438, 538, 540, 545, 549, 813, 818, 819, 825, 841, 843, 1049, 1050, 1069.

Example 14
*Spodoptera litoralis*

Larvae (L3) of the butterfly species *Spodoptera litoralis* were introduced into Petri dishes containing approximately 5 ml of an artificial diet and sprayed with an aqueous dilution of a wettable powder suspension of the test compounds at an application rate corresponding to 600 l/ha. The Petri dishes were then sealed and stored at room temperature for 5 days. The mortality of the animals which had been introduced was then determined. An activity of 100% was shown by the compounds of tabulated Examples 382 and 438.

Example 15
Ovicidal action (*Manduca sexta*)

Japan filter paper was placed on the inside of Petri dish bottoms, and 20 1-day-old eggs of *Manduca sexta* were transferred to the paper. Approximately 1 ml of an artificial insect diet was then placed in the middle of the Petri dish, and the inside of the bottom together with eggs and diet was sprayed with an aqueous wettable powder suspension of the test products corresponding to a rate of 600 l/ha. After the Petri dishes had been sealed and stored at room temperature for 5 days, the mortality of the eggs were determined. An activity of 100% was shown by the compounds of tabulated Examples: 360, 392, 412, 431, 533, 536, 539, 546, 549, 803, 815, 819, 843, 853, 1049.

Example 16
*Nilaparvata lugens*

Rice seed was germinated under moist conditions and grown in dishes to a height of approximately 10 cm. Batches of 3 rice plants were planted into glass tubes which had been filled with wet cottonwool, and the leaves of the rice plants were immersed in an aqueous dilution of a wettable powder concentrate comprising 250 ppm of the active substance in question. After the coating had dried on, the plants with the tubes were placed on the bottom of a dish, 10 specimens of the brown planthopper (*Nilaparvata lugens*, L3) were introduced into the dish, and the dish was sealed and stored at 25° C. The mortality of the planthoppers was checked after 3 days. A destruction of 100% was achieved using the compounds of tabulated Examples 382, 388, 399, 412, 424, 431, 438, 530, 538, 804, 813, 843, 855, 1050.

Ixodicidal Action

Example 17

In-vitro test on tropical cattle ticks (*Boophilus microplus*)

The following experimental set-up was used to demonstrate the activity of the compounds according to the invention against ticks: To prepare a suitable preparation of active substance, the active substances were dissolved in a mixture composed of dimethylformamide (85 g), nonylphenol polyglycol ether (3 g) and oxyethylated castor oil (7 g) to give a 10% (w/v) mixture, and the resulting emulsion concentrates were diluted with water to a test concentration of 500 ppm.

Batches of ten females of the tropical tick *Boophilus microplus* which have sucked themselves full were immersed for five minutes in these active substance dilutions. The ticks were subsequently dried on filter paper and then attached with their backs to an adhesive film in order to lay eggs. The ticks were kept in an incubator at 28° C. and an atmospheric humidity of 90%.

For control purposes, females ticks were immersed in plain water. The activity was assessed two weeks after the treatment on the basis of the inhibition of ovipositing.

In this test, ovi positing was inhited to 100% by each of the compounds of Example numbers 382, 392, 412, 431, 438, 530, 533, 536, 539, 546, 809, 819, 841, 843, 1049 at a concentration of active substance of 500 ppm.

C. PREPARATION EXAMPLES

Example A
(tabulated Example 817)

5-Chloro-4-(3,3-diethyl-1,5-dioxaspiro[5.5]undec-9-yloxy)-6-ethylpyrimidine 2.0 g (8.8 mmol) of 3,3-diethyl-1,5-dioxaspiro[5.5]-undecan-9-ol were added to a suspension of 0.80 g (13.2 mmol) of sodium hydride (80%) in 20 ml of dry THF under a nitrogen atmosphere and the mixture was refluxed for 2 hours until deprotonation was complete. The reaction solution was then allowed to cool to approximately 35° C., and 1.60 g (8.9 mmol) of 4,5-dichloro-6-ethylpyrimidine dissolved in 3 ml of dry THF were added rapidly, and the reaction mixture was refluxed until the reaction was complete (approximately 2 hours, TLC check). After the reaction mixture had cooled to room temperature, 3 ml of isopropanol were added to destroy excess sodium hydride, the mixture was stirred for a further 15 minutes and poured into a mixture of in each case 100 ml of ether and saturated aqueous ammonium chloride solution. The aqueous phase was extracted thoroughly using ether, and the combined organic phases were dried over magnesium sulfate and subsequently concentrated in vacuo. Silica gel chromatography (petroleum ether/ethyl acetate 3:2) gave 2.0 g (60.3% of theory) of a colorless oil.

Synthesis of the Alcohol Component 3,3-Diethyl-1,5-dioxaspiro[5.5]undecan-9-ol 820 mg (21.5 mmol) of sodium borohydride were added to a solution of 13 g (57.4 nmol) of 3,3-diethyl-1,5-dioxaspiro[5.5]undecan-9-one in 200 ml of ethanol and the mixture was stirred at room temperature for 1 hour. To complete the reaction, the mixture was heated at 40° C. for a further 15 hours. To destroy excess sodium borohydride, approximately 5 ml of acetone were added to the reaction solution and stirring was continued at 40° C. for a further 30 minutes. The reaction solution was subsequently concentrated in vacuo and the product taken up in ether and washed using ammonium chloride solution and water. The organic phase was dried carefully over magnesium sulfate and subsequently evaporated to dryness. This gave 11.8 g (90.0%) of the desired cyclohexanol. The crude product was further reacted without further purification.

3,3-Diethyl-1,5-dioxaspiro[5.5]undecan-9-one 30 g (0.27 mmol) of cyclohexane-1,4-dione, 35.4 g (0.27 mol) of 2,2-diethylpropane-1,3-diol and 360 mg of para-toluenesulfonic acid were heated in 200 ml of toluene on a water separator. After the mixture had been cooled to room temperature and the water of reaction separated off, the organic phase was washed with a semisaturated sodium hydrogen carbonate solution and dried over magnesium sulfate. After the solvent had been evaporated, 65 g of crude product were obtained which was purified by flash chromatography (ethyl acetate/petroleum ether=1:4). The first fraction contained the 1,4-diketal which was formed as secondary product (10 g). The main fraction contained 28.5 g (47%) of a yellow oil.

Example B
(Tabulated Example 804)

4-(3,3-Dimethyl-1,5-dioxaspiro[5.5]undec-9-ylamino)-5-methoxy-6-methoxymetthylpyrimidine 3.8 g (0.02 mol) of 4-chloro-5-methoxy-6-methoxymethylpyrimidine (Collection Czechoslov. Chem. Commun. 33 (1968), 2266), 5.0 g (0.025 mol) of 3,3-dimethyl-1,5-dioxaspiro[5.5]undec-9-ylamine and 2.5 g (0.025 mol) of triethylamine were heated, without solvent, at 90° for 3 hours. After the mixture had been cooled to room temperature, it was taken up in water/methylene chloride, and the organic phase was dried and concentrated. Chromatography (silica gel, ethyl acetate) gave 2.8 g (39.8% of theory) of a colorless oil which solidified gradually. M.p. 112°–114° C.

Preparation of the Amine Component 3,3-Dimethyl-1,5-dioxaspiro[5.5]undec-9-ylamine A solution of 20.0 g (0.1 mol) of 3,3-dimethyl-1,5-dioxaspiro[5.5]undecan-9-one in 250 ml of methanol which contained 38 g of ammonia was hydrogenated at 100° C. and a hydrogen pressure of 100 bar in the presence of 3 g of Raney nickel. The catalyst was filtered off and the solvent was stripped off in vacuo. The crude product was purified by means of a thin film evaporator (140° C./0.8 bar). This gave 16 g (80% of theory) of distillate which solidified upon standing.

M.p. 50°–51° C.

Example C
(Tabulated Example 530)

5-Chloro-4-(2-ethoxymethyl-1,4-dioxaspiro[4.5]dec-8-ylamino)-6-ethylpyrimidine 3.0 g (10 mmol) of 4-(5-chloro-6-ethylpyrimidin-4-ylamino)-cyclohexanone ethylene ketal and 10 ml of 3-ethoxypropane-1,2-diol together with 100 mg of p-toluenesulfonic acid hydrate were refluxed for 8 hours in 10 ml of toluene. The reaction mixture was extracted by stirring with dilute sodium hydroxide solution and water, the organic phase was dried, and the solvent was stripped off in vacuo. The crude product was purified by silica gel chromatography (eluent petroleum ether/ethyl acetate 3:2). This gave 2.0 g (56.3% of theory) of a colorless oil (diastereomer mixture).

Preparation of 4-(5-chloro-6-ethylpyrimidin-4-ylamino)-cyclohexanone ethylene ketal (starting material)

53.1 g (0.3 mol) of 4,5-dichloro-6-ethylpyridimine, 47.1 g (0.3 mol) of 4-aminocyclohexanone ethylene ketal (prepared from cyclohexane-1,4-dione monoethylene ketal by reductive amination with ammonia/hydrogen/Raney nickel, 100° C./100 bar, yield 90%) and 52 g of triethylamine are heated at 90° for 6 hours, without solvent. For working up, the mixture was extracted by stirring with water, and the organic phase was dried and concentrated in vacuo. Distillation on a thin film evaporator (135°/0.5 bar) gave 57.8 g (65% of theory) of a colorless product which solidified upon standing.

M.p.: 102°–103° C.

Example D
(Tabulated Examples 430, 431)

5-Chloro-6-ethyl-4-(2-phenyl-1,4-dioxaspiro[4.5]dec-8-ylamino)pyrimidine 3.8 g (15 mmol) of 4-(4-chloro-6-ethylpyrimidin-4-ylamino)cyclohexanone, 2.8 g (20 mmol) of phenylethylene glycol and 500 mg of p-toluenesulfonic acid hydrate were heated on a water separator in 200 ml of toluene. After the water of reaction had been separated off, the mixture was extracted by stirring twice with dilute sodium hydroxide solution and once with water. The organic phase was dried and concentrated. The crude product was chromatographed on silica gel (petroleum ether/ethyl acetate 1:1). This give first 0.78 g (13.9% of theory) of one diastereomer (colorless crystals, m.p. 105°–106° C.) with a relatively low biological activity and, after 1.5 g (26.7% of theory) of a mixed fraction, 1.2 g (21.4% of theory) of the other diastereomer (colorless oil) with a potent biological activity.

Preparation of 4-(4-chloro-6-ethylpyrimidin-4-ylamino)-cyclohexanone (starting material)

70 g (0.235 mol) of 4-(5-chloro-6-ethylpyrimidin-4-ylamino) cyclohexanone ethylene ketal (starting material for Example C) were stirred at 50° C. for 8 hours in a mixture of 250 ml of tetrahydrofuran and 250 ml of 2N hydrochloric acid. For work-up, the mixture was diluted with 250 ml of toluene, and the organic phase was extracted by stirring with sodium carbonate solution and water. Stripping off the solvent mixture gave 53.4 g (90% of theory) of product, which can be reacted without further purification.

M.p. 108°–110° C.

Example E
(Tabulated Examples 504, 505)

5-Chloro-6-ethyl-4-(2-hydroxymethyl-1,4-dioxaspiro[4.5]-dec-8-ylamino)pyrimidine 10.2 g (0.04 mol) of 4-(5-chloro-6-ethylpyridimin-4-ylamino)cyclohexanone ethylene ketal (Example C, starting material), 7.4 g (0.08 mol) of glycerol and 0.5 g of toluenesulfonic acid hydrate were heated in 100 ml of toluene on a water separator until the evolution of water had ceased. After the mixture had cooled to room temperature, it was extracted twice by stirring with dilute sodium hydroxide solution, and the organic phase was dried and concentrated. For purification and separation of the isomers, the crude product was chromatographed on silica gel (ethyl acetate as eluent). This gave first 3.0 g (22.9% of theory) of the pure isomer A (colorless crystals, m.p.: 109°–110° C.), then 1.8 g (13.7% of theory) of an isomer mixture A and finally 1.8 g (13.7% of theory) of isomer B (colorless crystals, m.p. 97°–98° C.).

Example F
(Tabulated Example 659)

5-Chloro-6-ethyl-4-[2-methylpyridine-5-oxymethyl)-1,4-dioxaspiro[4.5]dec-8-ylamino]pyrimidine 1.1 g (0.01 mol) of 3-hydroxy-6-methylpyrimidine, 3.3 g (0.01 mol) of 5-chloro-6-ethyl-4-(2-hydroxymethyl-1,4-dioxaspiro[4.5]dec-8-ylamino)pyrimidine (Example E) and 2.6 g (0.01 mol) of triphenylphosphine were introduced into 75 ml of tetrahydrofuran, and a solution of 1.8 g (0.01 mol) of diethyl azodicarboxylate in 10 ml of tetrahydrofuran was added dropwise at room temperature. Stirring was continued at room temperature for 4 hours, the mixture was concentrated, and the residue was stirred with diisopropyl ether. Solid triphenylphosphine oxide and diethyl hydrazinedicarboxylate were removed by filtration, the filtrate was concentrated, and the residue was chromatographed on silica gel (eluent: ethyl acetate). This gave 2.6 g (62% of theory) of colorless oil (isomer mixture).

Example G

5-Chloro-6-ethyl-4-(2-methylsulfonyloxymethyl-1,3-dioxaspiro[4.5]dec-8-ylamino)pyrimidine 1.8 g (5.5 mol) of 5-chloro-6-ethyl-4-(2-hydroxymethyl-1,4-dioxaspiro[4.5]dec-8-ylamino)pyrimidine (Example E, isomer mixture) were dissolved in 20 ml of pyridine, and a solution of 0.7 g (6.1 mmol) of methanesulfonyl chloride was added dropwise at 0° C. After the mixture had been left to stand overnight, it was poured onto ice, the pH was brought to 3–4 using concentrated hydrochloric acid, the mixture was extracted by stirring with dichloromethane, and the organic phase was dried and concentrated. This gave 1.9 g (85% of theory) of a colorless solid (isomer mixture).

Example H
(Tabulated Example 569)

5-Chloro-6-ethyl-4-[2-(4-methoxyphenoxymethyl)-1,4-dioxaspiro[4.5]dec-8-ylamino]pyrimidine 1.17 g (94 mmol) of 4-hydroxyanisole were added, a little at a time, to a suspension of 0.28 g (9.4 mmol) of 80% sodium hydride (dispersion in oil) in 25 ml of dimethylformamide, and the mixture was stirred until the evolution of hydrogen had ceased, a solution of 1.90 g (47 mmol) of 5-chloro-6-ethyl-4-(2-methylsulfonyloxymethyl-1,3-dioxaspiro[4.5]dec-8-ylamino)pyrimidine (Example G) in a small amount of dimethylformamide was subsequently added dropwise, and stirring of the mixture was continued at 100° C. for 6 hours. After the solvent had been stripped off, the mixture was taken up in water/dichloromethane and extracted by stirring with dilute sodium hydroxide solution and with water, and the organic phase was dried and concentrated. The crude product was chromatographed on silica gel (eluent ethyl acetate/methanol 9:1). This gave 1.3 g (68.6% of theory) of a colorless oil (isomer mixture).

Example I
(Tabulated Examples 266, 267)

5-Chloro-6-ethyl-4-(2-n-pentyl-1-oxaspiro[2.5]oct-6-ylamino)pyrimidine

A solution of 4.0 g (0.02 mol) of m-chloroperbenzoic acid (85% strength) in 25 ml of dichloromethane was slowly added dropwise at 0° C. to a solution of 6.4 g (0.02 mol) of 5-chloro-6-ethyl-4-(4-hexylidenecyclohexylamino)pyrimidine (WO 95 07894) in 25 ml of dichloromethane. Stirring of the mixture was continued at room temperature for 4 hours. After the mixture had been allowed to stand overnight, it was extracted by stirring with aqueous sodium hydrogen carbonate solution, and the organic phase was dried and concentrated. The crude product was chromatographed on silica gel (petroleum ether/ethyl acetate 4:1). First, 1.8 g (265.6% of theory) of the isomer having the higher $R_f$ value (0.62) were eluted (colorless crystals, m.p.: 41°–42° C.), followed by 1.2 g (18.2% of theory) of isomer mixture and 0.22 g (3.3% of theory) of the isomer having the lower $R_f$ value (0.53) as a colorless oil.

More compounds which can be prepared in accordance with the present invention are listed in the Tables which follow. Inasfar as diaistereomers are possible, the isomer first eluted during silica gel chromatography using ethyl acetate, petroleum ether/ethyl acetate or ethyl acetate/methanol mixtures is termed A in the Tables, the isomer eluted last is termed B and unseparated mixtures are termed G.

TABLE 1

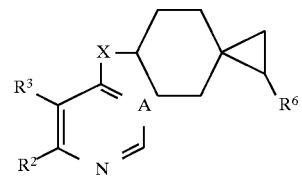

| Ex. No. | $R^2$ | $R^3$ | A | X | $R^6$ | Isomer | M.p. [°C.] |
|---|---|---|---|---|---|---|---|
| 1 | $C_2H_5$ | Cl | N | NH | H | — | |
| 2 | " | " | CH | " | " | — | |
| 3 | " | Br | N | " | " | — | |
| 4 | $CH_2OCH_2$ | $OCH_3$ | " | " | " | — | |
| 5 | $(CH_2)_4$ | " | " | O | " | — | |
| 6 | $C_2H_5$ | $OCH_3$ | CH | NH | " | — | |
| 7 | " | Cl | N | " | $CH_3$ | A | |
| 8 | " | " | " | " | " | B | |
| 9 | " | " | CH | " | " | A | |
| 10 | " | " | " | " | " | B | |
| 11 | " | Br | N | " | " | A | |
| 12 | " | " | " | " | " | B | |
| 13 | $CH_2OCH_3$ | $OCH_3$ | " | " | " | A | |
| 14 | " | " | " | " | " | B | |
| 15 | $C_2H_5$ | $OCH_3$ | CH | " | " | A | |
| 16 | " | " | " | " | " | B | |
| 17 | $(CH_2)_4$ | N | O | $CH_3$ | A | | |
| 18 | " | " | " | " | B | | |
| 19 | " | CH | NH | " | A | | |

TABLE 1-continued

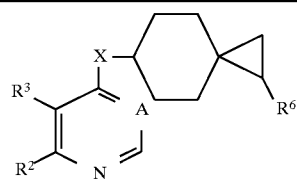

| Ex. No. | R² | R³ | A | X | R⁶ | Isomer | M.p. [°C.] |
|---|---|---|---|---|---|---|---|
| 20 |  | (CH₂)₄ | CH | NH | CH₃ | B |  |
| 21 | C₂H₅ | Cl | N | " | C₂H₅ | B |  |
| 22 | " | " | " | " | " | B |  |
| 23 | " | " | CH | " | " | A |  |
| 24 | " | " | " | " | " | B |  |
| 25 | C₂H₅ | Cl | N | NH | C₂H₅ | B |  |
| 26 | " | " | " | " | " | B |  |
| 27 | CH₂OCH₃ | OCH₃ | " | " | " | A |  |
| 28 | " | " | " | " | " | B |  |
| 29 | C₂H₅ | " | CH | " | " | A |  |
| 30 | " | " | " | " | " | B |  |
| 31 |  | (CH₂)₄ | N | O | " | A |  |
| 32 |  | " | " | " | " | B |  |
| 33 | C₂H₅ | Cl | " | NH | n-C₃H₇ | A |  |
| 34 | " | " | " | " | " | B |  |
| 35 | " | " | CH | " | " | A |  |
| 36 | " | " | " | " | " | B |  |
| 37 | CH₂OCH₃ | OCH₃ | N | " | " | A |  |
| 38 | " | " | " | " | " | B |  |
| 39 | C₂H₅ | OCH₃ | CH | NH | n-C₃H₇ | A |  |
| 40 | C₂H₅ | OCH₃ | CH | NH | n-C₃H₇ | B |  |
| 41 |  | (CH₂)₄ | N | O | " | A |  |
| 42 |  | " | " | " | " | B |  |
| 43 |  | (CH₂)₄ | CH | NH | n-C₃H₇ | A |  |
| 44 |  | (CH₂)₄ | CH | NH | n-C₃H₇ | B |  |
| 45 | C₂H₅ | Cl | N | " | i-C₃H₇ | A |  |
| 46 | " | " | " | " | " | B |  |
| 47 | Cl | " | CH | " | " | A |  |
| 48 | " | " | " | " | " | B |  |
| 49 | C₂H₅ | Br | N | " | " | A |  |
| 50 | C₂H₅ | Br | N | NH | i-C₃H₇ | B |  |
| 51 | CH₂OCH₃ | OCH₃ | " | " | " | A |  |
| 52 | " | " | " | " | " | B |  |
| 53 | C₂H₅ | " | CH | " | " | A |  |
| 54 | " | " | " | " | " | B |  |
| 55 |  | (CH₂)₄ | N | O | " | A |  |
| 56 |  | " | " | " | " | B |  |
| 57 | C₂H₅ | Cl | " | NH | n-C₄H₉ | A |  |
| 58 | C₂H₅ | Cl | N | NH | n-C₄H₉ | B |  |
| 59 | " | " | CH | " | " | A |  |
| 60 | C₂H₅ | Cl | CH | NH | n-C₄H₉ | B |  |
| 61 |  | (CH₂)₄ | N | O | " | A |  |
| 62 |  | (CH₂)₄ | " | " | " | B |  |
| 63 | C₂H₅ | Cl | " | NH | n-C₅H₁₁ | A |  |
| 64 | " | " | " | " | " | B |  |
| 65 | " | " | CH | " | " | A |  |
| 66 | C₂H₅ | Cl | CH | NH | n-C₅H₁₁ | B |  |
| 67 |  | (CH₂)₄ | N | O | " | A |  |
| 68 |  | (CH₂)₄ | N | O | n-C₅H₁₁ | B |  |
| 69 | C₂H₅ | Cl | " | NH | n-C₈H₁₇ | A |  |
| 70 | " | " | " | " | " | B |  |
| 71 | " | " | CH | " | " | A |  |
| 72 | " | " | " | " | " | B |  |
| 73 | " | " | N | NH | tert-C₄H₉ | A |  |
| 74 | " | " | " | " | " | B |  |
| 75 | " | " | " | " | phenyl | A |  |
| 76 | " | " | " | " | " | B |  |
| 77 | C₂H₅ | Cl | CH | NH | phenyl | A |  |
| 78 | " | " | " | " | " | B |  |
| 79 | C₂H₅ | Br | N | " | " | A |  |
| 80 | C₂H₅ | Br | N | NH | phenyl | B |  |
| 81 | CH₂OCH₃ | OCH₃ | " | " | " | A |  |
| 82 | " | " | " | " | " | B |  |
| 83 | C₂H₅ | OCH₃ | CH | NH | phenyl | A |  |
| 84 | " | " | " | " | " | B |  |
| 85 |  | (CH₂)₄ | N | O | " | A |  |
| 86 |  | " | " | " | " | B |  |

TABLE 1-continued

| Ex. No. | R² | R³ | A | X | R⁶ | Isomer | M.p. [°C.] |
|---|---|---|---|---|---|---|---|
| 87 | C₂H₅ | Cl | " | NH | 4-CH₃—C₆H₄ | A | |
| 88 | " | " | " | " | " | B | |
| 89 | C₂H₅ | Cl | CH | NH | 4-CH₃—C₆H₄ | A | |
| 90 | " | " | " | " | " | B | |
| 91 | CH₂OCH₃ | OCH₃ | N | " | " | A | |
| 92 | CH₂OCH₃ | OCH₃ | N | NH | 4-CH₃—C₆H₄ | B | |
| 93 | C₂H₅ | " | CH | " | " | A | |
| 94 | " | " | " | " | " | B | |
| 95 | | (CH₂)₄ | N | O | " | A | |
| 96 | | (CH₂)₄ | " | O | 4-CH₃—C₆H₄ | B | |
| 97 | C₂H₅ | Cl | " | NH | 4-F—C₆H₄ | A | |
| 98 | " | " | " | " | " | B | |
| 99 | " | " | CH | " | " | A | |
| 100 | C₂H₅ | Cl | CH | NH | 4-F—C₆H₄ | B | |
| 101 | | (CH₂)₄ | N | O | " | A | |
| 102 | | " | " | " | " | B | |
| 103 | C₂H₅ | Cl | " | NH | 4-Cl—C₆H₄ | A | |
| 104 | " | " | " | " | " | B | |
| 105 | " | " | CH | " | " | A | |
| 106 | " | " | " | " | " | B | |
| 107 | | (CH₂)₄ | N | O | " | A | |
| 108 | | " | " | " | " | B | |
| 109 | C₂H₅ | Cl | " | NH | 4-CF₃—C₆H₄ | A | |
| 110 | " | " | " | " | " | B | |
| 111 | " | " | CH | " | " | A | |
| 112 | C₂H₅ | Cl | CH | NH | 4-CF₃—C₆H₄ | B | |
| 113 | | (CH₂)₄ | N | O | " | A | |
| 114 | | " | " | " | " | B | |
| 115 | C₂H₅ | Cl | N | NH | 4-CH₃O—C₆H₄ | A | |
| 116 | C₂H₅ | Cl | N | NH | 4-CH₃O—C₆H₄ | B | |
| 117 | " | " | CH | " | " | A | |
| 118 | " | " | " | " | " | B | |
| 119 | | (CH₂)₄ | N | O | " | A | |
| 120 | | (CH₂)₄ | N | O | 4-CH₃O—C₆H₄ | B | |
| 121 | C₂H₅ | Cl | N | NH | 4-C₂H₅O—C₆H₄ | A | |
| 122 | " | " | " | " | " | B | |
| 123 | " | " | CH | " | " | A | |
| 124 | " | " | " | " | " | B | |
| 125 | | (CH₂)₄ | N | O | " | A | |
| 126 | | " | " | " | " | B | |
| 127 | C₂H₅ | Cl | " | NH | 4-(CH₃)₃COOC—C₆H₄ | A | |
| 128 | " | " | " | " | " | B | |
| 129 | " | " | CH | " | " | A | |
| 130 | " | " | " | " | " | B | |
| 131 | | (CH₂)₄ | N | O | " | A | |
| 132 | | " | " | " | " | B | |
| 133 | C₂H₅ | Cl | " | NH | 2-thienyl | A | |
| 134 | C₂H₅ | Cl | N | NH | 2-thienyl | B | |
| 135 | C₂H₅ | Cl | CH | N | 2-thienyl | A | |
| 136 | " | " | " | " | " | B | |
| 137 | | (CH₂)₄ | N | O | " | A | |
| 138 | | " | " | " | " | B | |
| 139 | C₂H₅ | Cl | " | NH | benzyl | A | |
| 140 | C₂H₅ | Cl | N | NH | benzyl | B | |
| 141 | " | " | CH | " | " | A | |
| 142 | " | " | " | " | " | B | |
| 143 | | (CH₂)₄ | N | O | " | A | |
| 144 | | " | " | " | " | B | |

TABLE 2

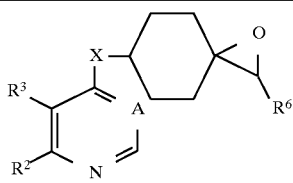

| Ex. No. | R² | R³ | A | X | U | R⁶ | Isomer | M.p. [°C.] |
|---|---|---|---|---|---|---|---|---|
| 145 | C₂H₅ | Cl | N | NH | — | cyclopropyl | A | |
| 146 | " | " | " | " | — | " | B | |
| 147 | " | " | " | " | — | cyclohexyl | A | |
| 148 | " | " | " | " | — | " | B | |
| 149 | " | " | " | " | — | 1,3-dioxolan-2-yl | A | |
| 150 | " | " | " | " | — | " | B | |
| 151 | " | " | " | " | — | 1,3-dioxan-2-ylmethyl | A | |
| 152 | " | " | " | " | — | " | B | |
| 153 | " | " | " | " | — | trimethylsilyl | A | |
| 154 | " | " | " | " | — | " | B | |
| 155 | " | " | " | " | — | —CH=CH₂ | A | |
| 156 | " | " | " | " | — | " | B | |
| 157 | " | " | " | " | — | —C≡CH | A | |
| 158 | " | " | " | " | — | " | B | |
| 159 | " | " | " | " | — | —C≡C—Si(CH₃)₃ | A | |
| 160 | " | " | " | " | — | " | B | |
| 161 | " | " | " | " | O | CH₃ | A | |
| 162 | " | " | " | " | " | " | B | |
| 163 | " | " | " | " | " | C₆H₅ | A | |
| 164 | C₂H₅ | Cl | N | NH | O | C₆H₅ | B | |
| 165 | " | " | " | " | S | CH₃ | A | |
| 166 | " | " | " | " | " | " | B | |
| 167 | " | " | " | " | " | C₆H₅ | A | |
| 168 | " | " | " | " | " | " | B | |

TABLE 3

| Ex. No. | R² | R³ | A | X | R⁶ | Isomer | M.p. [°C.] |
|---|---|---|---|---|---|---|---|
| 200 a | C₂H₅ | Cl | N | NH | H | A | |
| 200 b | | | | | | B | |
| 201 a | " | " | CH | " | " | A | |
| 201 b | | | | | | B | |
| 202 a | " | Br | N | " | " | A | |
| 202 b | | | | | | B | |
| 203 a | CH₂OCH₃ | OCH₃ | " | " | " | A | |
| 203 b | | | | | | B | |
| 204 a | C₂H₅ | " | CH | " | " | A | |
| 204 b | | | | | | B | |
| 205 | | (CH₂)₄ | N | O | " | A | |
| | | | | | | B | |
| 206 | C₂H₅ | Cl | " | NH | CH₃ | A | |
| 207 | " | " | " | " | " | B | |
| 208 | " | " | CH | " | " | A | |
| 209 | " | " | " | " | " | B | |
| 210 | " | Br | N | " | " | A | |
| 211 | " | " | " | " | " | B | |
| 212 | CH₂OCH₃ | OCH₃ | " | " | " | A | |
| 213 | " | " | " | " | " | B | |
| 214 | C₂H₅ | " | CH | " | " | A | |
| 215 | " | " | " | " | " | B | |
| 216 | | (CH₂)₄ | N | O | " | A | |
| 217 | | " | " | " | " | B | |
| 218 | C₂H₅ | Cl | " | NH | C₂H₅ | A | |
| 219 | C₂H₅ | Cl | N | NH | C₂H₅ | B | |

TABLE 3-continued

| Ex. No. | R² | R³ | A | X | R⁶ | Isomer | M.p. [°C.] |
|---|---|---|---|---|---|---|---|
| 220 | " | " | CH | " | " | A | |
| 221 | " | " | " | " | " | B | |
| 222 | C₂H₅ | Br | N | NH | C₂H₅ | A | |
| 223 | " | " | " | " | " | B | |
| 224 | CH₂OCH₃ | OCH₃ | N | NH | C₂H₅ | A | |
| 225 | " | " | " | " | " | B | |
| 226 | C₂H₅ | " | CH | " | " | A | |
| 227 | " | " | " | " | " | B | |
| 228 | (CH₂)₄ | | N | O | " | A | |
| 229 | " | | " | " | " | B | |
| 230 | C₂H₅ | Cl | " | NH | n-C₃H₇ | A | |
| 231 | " | " | " | " | " | B | |
| 232 | " | " | CH | " | " | A | |
| 233 | " | " | " | " | " | B | |
| 234 | " | Br | N | " | " | A | |
| 235 | " | " | " | " | " | B | |
| 236 | CH₂OCH₃ | OCH₃ | " | " | " | A | |
| 237 | " | " | " | " | " | B | |
| 238 | C₂H₅ | OCH₃ | CH | NH | n-C₃H₇ | A | |
| 239 | " | " | " | " | " | B | |
| 240 | (CH₂)₄ | | N | O | " | A | |
| 241 | " | | " | " | " | B | |
| 242 | C₂H₅ | Cl | N | NH | i-C₃H₇ | A | |
| 243 | " | " | " | " | " | B | |
| 244 | " | " | CH | " | " | A | |
| 245 | " | " | " | " | " | B | |
| 246 | " | Br | N | " | " | A | |
| 247 | " | " | " | " | " | B | |
| 248 | CH₂OCH₃ | OCH₃ | N | NH | i-C₃H₇ | A | |
| 249 | " | " | " | " | " | B | |
| 250 | C₂H₅ | " | CH | " | " | A | |
| 251 | " | " | " | " | " | B | |
| 252 | (CH₂)₄ | | N | O | " | A | |
| 253 | " | | " | " | " | B | |
| 254 | C₂H₅ | Cl | " | NH | n-C₄H₉ | A | |
| 255 | C₂H₅ | Cl | N | NH | n-C₄H₉ | B | |
| 256 | " | " | CH | " | " | A | |
| 257 | C₂H₅ | Cl | CH | NH | n-C₄H₉ | B | |
| 258 | (CH₂)₄ | | N | O | " | A | |
| 259 | " | | " | " | " | B | |
| 260 | C₂H₅ | Cl | " | NH | tert-C₄H₉ | A | |
| 261 | " | " | " | " | " | B | |
| 262 | " | " | CH | " | " | A | |
| 263 | " | " | " | " | " | B | |
| 264 | (CH₂)₄ | | N | O | " | A | |
| 265 | (CH₂)₄ | | N | O | tert-C₄H₉ | B | |
| 266 | C₂H₅ | Cl | " | NH | n-C₅H₁₁ | A | 41–42 |
| 267 | " | " | " | " | " | B | oil |
| 268 | " | " | CH | " | " | A | |
| 269 | " | " | " | " | " | B | |
| 270 | " | " | N | " | n-C₆H₁₃ | A | |
| 271 | " | " | " | " | " | B | |
| 272 | " | " | CH | " | " | A | |
| 273 | " | " | " | " | " | B | |
| 274 | " | " | N | " | n-C₈H₁₇ | A | |
| 275 | " | " | " | " | " | B | |
| 276 | C₂H₅ | Cl | CH | NH | n-C₈H₁₇ | A | |
| 277 | " | " | " | " | " | B | |
| 278 | " | " | N | " | C₆H₅ | G | resin |
| 279 | " | " | " | " | " | B | |
| 280 | " | " | CH | " | " | A | |
| 281 | " | " | " | " | " | B | |
| 282 | " | Br | N | " | " | A | |
| 283 | " | " | " | " | " | B | |
| 284 | CH₂OCH₃ | OCH₃ | " | " | " | A | |
| 285 | " | " | " | " | " | B | |
| 286 | C₂H₅ | " | CH | " | " | A | |

TABLE 3-continued

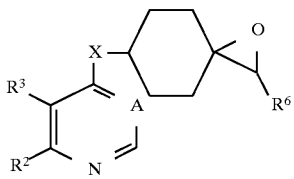

| Ex. No. | R² | R³ | A | X | R⁶ | Isomer | M.p. [°C.] |
|---|---|---|---|---|---|---|---|
| 287 | " | " | " | " | " | B | |
| 288 | | (CH₂)₄ | N | O | C₆H₅ | A | |
| 289 | | " | " | " | " | B | |
| 290 | C₂H₅ | Cl | " | NH | 4-Cl—C₆H₄ | A | |
| 291 | " | " | " | " | " | B | |
| 292 | " | " | " | " | 4-F—C₆H₄ | A | |
| 293 | " | " | " | " | " | B | |
| 294 | " | " | " | " | 4-CH₃—C₆H₄ | A | |
| 295 | C₂H₅ | Cl | N | NH | 4-CH₃—C₆H₄ | B | |
| 296 | C₂H₅ | Cl | N | NH | 4-CH₃—O—C₆H₄ | A | |
| 297 | " | " | " | " | " | B | |
| 298 | " | " | " | " | 4-C₂H₅O—C₆H₄ | A | |
| 299 | " | " | " | " | " | B | |
| 300 | " | " | " | " | 4-(CH₃)₃COOC—C₆H₄ | A | |
| 301 | " | " | " | " | " | B | |
| 302 | " | " | " | " | 2-thienyl | A | |
| 303 | " | " | " | " | " | B | |
| 304 | " | " | " | " | benzyl | A | |
| 305 | " | " | " | " | " | B | |
| 306 | " | " | " | " | cyclopropyl | A | |
| 307 | " | " | " | " | " | B | |
| 308 | " | " | " | " | cyclohexyl | A | |
| 309 | " | " | " | " | " | B | |
| 310 | " | " | " | " | 1,3-dioxolan-2-yl | A | |
| 311 | C₂H₅ | Cl | N | NH | 1,3-dioxan-2-ylmethyl | B | |
| 312 | " | " | " | " | " | A | |
| 313 | " | " | " | " | " | B | |
| 314 | C₂H₅ | Cl | N | NH | trimethylsilyl | A | |
| 315 | " | " | " | " | " | B | |
| 316 | " | " | " | " | CH=CH₂ | A | |
| 317 | " | " | " | " | " | B | |
| 318 | " | " | " | " | —C≡CH | A | |
| 319 | " | " | " | " | " | B | |

TABLE 4

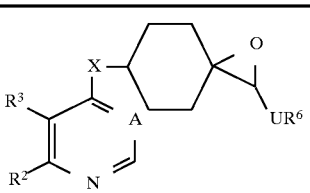

| Ex. No. | R² | R³ | A | X | U | R⁶ | Isomer | M.p. [°C.] |
|---|---|---|---|---|---|---|---|---|
| 320 | C₂H₅ | Cl | N | NH | — | —C≡C—Si(CH₃)₃ | A | |
| 322 | " | " | " | " | — | " | B | |
| 323 | " | " | " | " | O | CH₃ | A | |
| 324 | " | " | " | " | " | " | B | |
| 325 | " | " | " | " | " | C₆H₅ | A | |
| 326 | " | " | " | " | " | " | B | |

TABLE 5

[Structure: cyclohexane-dioxolane with pyridine ring bearing R², R³, X, A substituents; dioxolane has R⁵, R⁶]

| Ex. No. | R² | R³ | A | X | R⁵ | R⁶ | Isomer | M.p. [°C.] |
|---|---|---|---|---|---|---|---|---|
| 350 | C₂H₅ | Cl | N | NH | H | CH₃ | A | |
| 351 | " | " | " | " | " | " | B | |
| 352 | " | " | " | " | " | " | G | oil |
| 353 | " | " | CH | " | " | " | A | |
| 354 | " | " | " | " | " | " | B | |
| 355 | CH₂OCH₃ | OCH₃ | N | " | " | " | A | |
| 356 | " | " | " | " | " | " | B | |
| 357 | (CH₂)₄ | | " | O | " | " | A | |
| 358 | " | | " | " | " | " | B | |
| 359 | C₂H₅ | Cl | " | NH | ▷CH₃ | ▷CH₃ | — | 62–63 |
| 360 | CH₂OCH₃ | OCH₃ | " | " | " | " | — | 107–108 |
| 361 | C₂H₅ | Cl | " | " | " | . . . CH₃ | — | 58–59 |
| 362 | CH₂OCH₃ | OCH₃ | " | " | " | " | — | 86–87 |
| 363 | C₂H₅ | Cl | " | " | H | C₂H₅ | A | |
| 364 | " | " | " | " | " | " | B | |
| 365 | " | " | CH | " | " | " | A | |
| 366 | " | " | " | " | " | " | B | |
| 367 | CH₂OCH₃ | OCH₃ | N | NH | H | C₂H₅ | A | |
| 368 | " | " | " | " | " | " | B | |
| 369 | C₂H₅ | Cl | N | NH | H | n-C₃H₇ | A | |
| 370 | " | " | " | " | " | " | B | |
| 371 | " | " | CH | " | " | " | A | |
| 372 | " | " | " | " | " | " | B | |
| 373 | CH₂OCH₃ | OCH₃ | N | " | " | " | A | |
| 374 | " | " | " | " | " | " | B | |
| 375 | C₂H₅ | Cl | N | NH | H | i-C₃H₇ | A | |
| 376 | " | " | " | " | " | " | B | |
| 377 | " | " | CH | " | " | " | A | |
| 378 | " | " | " | " | " | " | B | |
| 379 | CH₂OCH₃ | OCH₃ | N | " | " | " | A | |
| 380 | " | " | " | " | " | " | B | |
| 381 | C₂H₅ | Cl | " | " | " | n-C₄H₉ | A | oil |
| 382 | " | " | " | " | " | " | B | oil |
| 383 | " | " | CH | " | " | " | A | |
| 384 | " | " | " | " | " | " | B | |
| 385 | CH₂OCH₃ | OCH₃ | N | " | " | " | A | |
| 386 | CH₂OCH₃ | OCH₃ | N | NH | H | n-C₄H₉ | B | |
| 387 | " | " | " | O | " | " | A | oil |
| 388 | " | " | " | " | " | " | B | oil |
| 389 | C₂H₅ | Br | " | NH | " | " | A | |
| 390 | " | " | " | " | " | " | B | |
| 391 | " | Cl | " | " | " | tert-C₄H₉ | A | 94–95 |
| 392 | C₂H₅ | Cl | N | NH | H | tert-C₄H₉ | B | oil |
| 393 | " | " | CH | " | " | " | A | |
| 394 | " | " | " | " | " | " | B | |
| 395 | " | Br | N | " | " | " | A | |
| 396 | " | " | " | " | " | " | B | |
| 397 | CH₂OCH₃ | OCH₃ | " | " | " | " | A | |
| 398 | " | " | " | " | " | " | B | |
| 399 | " | " | " | " | " | " | G | oil |
| 400 | C₂H₅ | OCH₃ | CH | N | H | tert-C₄H₉ | A | |
| 401 | " | " | " | " | " | " | B | |
| 402 | (CH₂)₄ | | N | O | " | " | A | |
| 403 | " | | " | " | " | " | B | |
| 404 | C₂H₅ | Cl | " | NH | " | n-C₆H₁₃ | A | oil |
| 405 | C₂H₅ | Cl | N | NH | H | n-C₆H₁₃ | B | oil |
| 406 | " | " | CH | " | " | " | A | |
| 407 | " | " | " | " | " | " | B | |
| 408 | C₂H₅ | Br | N | NH | H | n-C₆H₁₃ | A | |
| 409 | C₂H₅ | Br | N | NH | H | n-C₆H₁₃ | B | |
| 410 | CH₂OCH₃ | OCH₃ | " | " | " | " | A | |
| 411 | " | " | " | " | " | " | B | |
| 412 | " | " | " | " | " | " | G | oil |
| 413 | (CH₂)₄ | | " | O | " | " | A | |
| 414 | " | | " | " | " | " | B | |
| 415 | C₂H₅ | Cl | N | NH | H | n-C₈H₁₇ | A | oil |

TABLE 5-continued

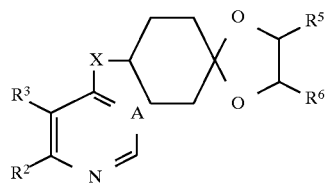

| Ex. No. | R² | R³ | A | X | R⁵ | R⁶ | Isomer | M.p. [°C.] |
|---|---|---|---|---|---|---|---|---|
| 416 | " | " | " | " | " | " | B | oil |
| 417 | " | " | CH | " | " | " | A | |
| 418 | " | " | " | " | " | " | B | |
| 419 | " | Br | N | " | " | " | A | |
| 420 | " | " | " | " | " | " | B | |
| 422 | CH₂OCH₃ | OCH₃ | " | " | " | " | A | |
| 423 | " | " | " | " | " | " | B | |
| 424 | " | " | " | " | " | " | G | oil |
| 425 | | (CH₂)₄ | N | O | H | n-C₈H₁₇ | A | |
| 426 | | " | " | " | " | " | B | |
| 427 | C₂H₅ | Cl | N | NH | | ▷(CH₂)₃◁ | — | 99–100 |
| 428 | " | " | " | " | | ▷(CH₂)₄◁ | — | oil |
| 429 | " | " | " | " | | ▷(CH₂)₄ . . . | — | oil |
| 430 | " | " | " | " | H | phenyl | A | 105–106 |
| 431 | " | " | " | " | " | " | B | oil |
| 432 | " | " | CH | " | " | " | A | |
| 433 | " | " | " | " | " | " | B | |
| 434 | " | Br | N | " | " | " | A | |
| 435 | " | " | " | " | " | " | B | |
| 436 | CH₂OCH₃ | OCH₃ | " | " | " | " | A | |
| 437 | " | " | " | " | " | " | B | |
| 438 | " | " | " | " | " | " | G | oil |
| 439 | C₂H₅ | OCH₃ | CH | NH | H | phenyl | A | |
| 440 | " | " | " | " | " | " | B | |
| 441 | | (CH₂)₄ | N | O | " | " | A | |
| 442 | | (CH₂)₄ | N | O | H | phenyl | B | |
| 443 | C₂H₅ | Cl | N | NH | " | 4-F—C₆H₄ | A | |
| 444 | C₂H₅ | Cl | N | NH | H | 4-F—C₆H₄ | B | |
| 445 | " | " | CH | " | " | " | A | |
| 446 | " | " | " | " | " | " | B | |
| 447 | " | " | N | " | " | 4-Cl—C₆H₄ | A | |
| 448 | " | " | " | " | " | " | B | |
| 449 | C₂H₅ | Cl | CH | NH | " | 4-Cl—C₆H₄ | A | |
| 450 | " | " | " | " | " | " | B | |
| 451 | " | " | N | " | " | 4-CH₃—C₆H₄ | A | |
| 452 | " | " | " | " | " | " | B | |
| 453 | " | " | CH | " | " | " | A | |
| 454 | " | " | " | " | " | " | B | |
| 455 | " | " | N | " | " | 4-(CH₃)₃C—C₆H₄ | A | |
| 456 | " | " | " | " | " | " | B | |
| 457 | " | " | CH | " | " | " | A | |
| 458 | " | " | " | " | " | " | B | |
| 459 | " | " | N | " | " | 4-CH₃O—C₆H₄ | G | oil |
| 460 | " | " | " | " | " | " | B | |
| 461 | " | " | CH | " | " | " | A | |
| 462 | C₂H₅ | Cl | CH | NH | H | 4-CH₃O—C₆H₄ | B | |
| 463 | CH₂OCH₃ | OCH₃ | N | NH | H | 4-CH₃O—C₆H₄ | A | |
| 464 | " | " | " | " | " | " | B | |
| 465 | " | " | " | O | " | " | A | |
| 466 | " | " | " | " | " | " | B | |
| 467 | C₂H₅ | Cl | " | NH | " | 4-C₂H₅O—C₆H₄ | A | |
| 468 | " | " | " | " | " | " | B | |
| 469 | " | " | CH | " | " | " | A | |
| 470 | " | " | " | " | " | " | B | |
| 471 | CH₂OCH₃ | OCH₃ | N | " | " | " | — | |
| 472 | " | " | " | " | " | " | — | |
| 473 | C₂H₅ | Cl | N | NH | H | 3,4-dimethoxyphenyl | A | |
| 474 | " | " | " | " | " | " | B | |
| 475 | C₂H₅ | Cl | CH | NH | H | 3,4-dimethoxyphenyl | A | |
| 476 | C₂H₄ | Cl | CH | NH | H | 3,4-dimethoxyphenyl | B | |
| 478 | CH₂OCH₃ | OCH₃ | N | " | " | " | A | |
| 479 | " | " | " | " | " | " | B | |
| 480 | C₂H₅ | Cl | " | " | " | 2-thienyl | A | |
| 481 | " | " | " | " | " | " | B | |
| 482 | C₂H₅ | Cl | CH | NH | H | 2-thienyl | A | |
| 483 | " | " | " | " | " | " | B | |

TABLE 5-continued

[Structure shown: cyclohexane with dioxolane bearing R⁵ and R⁶, linked via X to a pyridine/pyrimidine ring with R², R³, and A]

| Ex. No. | R² | R³ | A | X | R⁵ | R⁶ | Isomer | M.p. [°C.] |
|---|---|---|---|---|---|---|---|---|
| 484 | " | " | N | " | " | 2-pyridyl | A | |
| 485 | " | " | " | " | " | " | B | |
| 486 | C₂H₅ | Cl | CH | N | NH | 2-pyridyl | A | |
| 487 | " | " | " | " | " | " | B | |
| 488 | CH₂OCH₃ | OCH₃ | N | " | " | " | A | |
| 489 | " | " | " | " | " | " | B | |
| 490 | C₂H₅ | " | " | " | " | 3-pyridyl | A | |
| 491 | " | " | " | " | " | " | B | |
| 492 | " | " | CH | " | " | " | A | |
| 493 | " | " | " | " | " | " | B | |
| 494 | CH₂OCH₃ | OCH₃ | N | " | " | " | A | |
| 495 | " | " | " | " | " | " | B | |
| 496 | C₂H₅ | Cl | " | " | " | 4-pyridyl | A | |
| 497 | " | " | " | " | " | " | B | |
| 498 | " | " | CH | " | " | " | A | |
| 499 | " | " | " | " | " | " | B | |
| 500 | CH₂OCH₃ | OCH₃ | N | " | " | " | A | |
| 501 | CH₂OCH₃ | OCH₃ | N | NH | H | 4-pyridyl | B | |
| 502 | C₂H₅ | Cl | N | NH | H | CH₂—(CF₂)₅CF₃ | A | 77–78 |
| 503 | " | " | " | " | " | " | B | oil |
| 504 | " | " | " | " | " | CH₂OH | A | 97–98 |
| 505 | " | " | " | " | " | " | B | 109–110 |
| 506 | " | " | CH | " | " | " | A | |
| 507 | " | " | " | " | " | " | B | |
| 508 | " | Br | N | " | " | " | A | |
| 509 | C₂H₅ | Br | N | NH | H | CH₂OH | B | |
| 510 | CH₂OCH₃ | OCH₃ | " | " | " | " | A | |
| 511 | " | " | " | " | " | " | B | |
| 512 | C₂H₅ | " | CH | " | " | " | A | |
| 513 | " | " | " | " | " | " | B | |
| 514 | (CH₂)₄ | | N | O | " | " | A | |
| 515 | " | | " | " | " | " | B | |
| 516 | C₂H₅ | Cl | " | NH | " | CH₂OSO₂CH₃ | A | |
| 517 | " | " | " | " | " | " | B | |
| 518 | " | " | " | " | " | 4-toluenesulfonyl-oxymethyl | A | |
| 519 | " | " | " | " | " | 4-toluenesulfonyl-oxymethyl | B | |
| 520 | C₂H₅ | Cl | N | NH | H | CH₂OCH₃ | A | |
| 521 | " | " | " | " | " | " | B | |
| 522 | " | " | CH | " | " | " | A | |
| 523 | " | " | " | " | " | " | B | |
| 524 | CH₂OCH₃ | OCH₃ | N | " | " | " | A | |
| 525 | " | " | " | " | " | " | B | |
| 526 | (CH₂)₄ | | " | O | " | " | A | |
| 527 | " | | " | " | " | " | B | |
| 528 | C₂H₅ | Cl | N | NH | " | CH₂OC₂H₅ | A | |
| 529 | " | " | " | " | " | " | B | |
| 530 | " | " | " | " | " | " | G | oil |
| 531 | " | " | " | O | " | " | A | |
| 532 | C₂H₅ | Cl | N | O | H | CH₂OC₂H₅ | B | |
| 533 | " | " | " | " | " | " | G | oil |
| 534 | " | " | CH | NH | " | " | A | |
| 535 | " | " | " | " | " | " | B | |
| 536 | CH₂OCH₃ | " | N | " | " | " | G | oil |
| 537 | " | " | " | O | " | " | G | oil |
| 538 | (CH₂)₄ | | " | " | " | " | G | oil |
| 539 | C₂H₅ | Cl | N | NH | H | CH₂OC(CH₃)₃ | G | oil |
| 540 | " | " | " | O | " | " | G | oil |
| 541 | C₂H₅ | Cl | CH | NH | H | CH₂OC(CH₃)₃ | A | |
| 542 | C₂H₅ | Cl | CH | NH | H | CH₂OC—(CH₃)₃ | B | |
| 543 | CH₂OCH₃ | OCH₃ | N | " | " | " | G | oil |
| 544 | " | " | " | O | " | " | G | oil |
| 545 | (CH₂)₄ | | " | " | " | " | G | oil |
| 546 | C₂H₅ | Cl | N | NH | H | CH₂SC₂H₅ | G | oil |
| 547 | " | " | " | " | " | CH₂O—CH₂—C₆H₅ | A | |

TABLE 5-continued

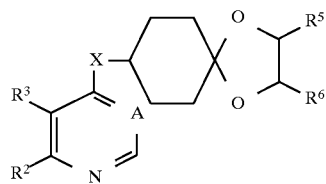

| Ex. No. | $R^2$ | $R^3$ | A | X | $R^5$ | $R^6$ | Isomer | M.p. [°C.] |
|---|---|---|---|---|---|---|---|---|
| 548 | " | " | " | " | " | " | B | |
| 549 | " | " | " | " | " | " | G | oil |
| 550 | " | " | CH | " | " | " | A | |
| 551 | " | " | " | " | " | " | B | |
| 552 | $CH_2OCH_3$ | $OCH_3$ | N | " | " | " | A | |
| 553 | " | " | " | " | " | " | B | |
| 554 | " | " | " | " | " | " | G | oil |
| 555 | $C_2H_5$ | Cl | N | NH | H | $C_6H_5$—$OCH_2$— | A | |
| 556 | " | " | " | " | " | " | B | resin |
| 557 | " | " | CH | " | " | " | A | |
| 558 | $C_2H_5$ | Cl | CH | NH | H | $C_6H_5O$—$OCH_2$— | B | |
| 559 | $CH_2OCH_3$ | $OCH_3$ | N | " | " | " | A | |
| 560 | " | " | " | " | " | " | B | |
| 561 | $C_2H_5$ | Cl | " | " | " | 4-$CH_3$—$C_6H_4$—$OCH_2$— | A | |
| 562 | " | " | " | " | " | " | B | resin |
| 563 | " | " | CH | " | " | " | A | |
| 564 | " | " | " | " | " | " | B | |
| 565 | " | " | N | " | " | 4-$(CH_3)_3C$—$C_6H_4$—$OCH_2$ | A | |
| 566 | " | " | " | " | " | " | B | |
| 567 | " | " | CH | " | " | " | A | |
| 568 | " | " | " | " | " | " | B | |
| 569 | " | " | N | " | " | 4-$CH_3O$—$C_6H_4$—$OCH_2$— | G | oil |
| 570 | " | " | " | " | " | " | B | |
| 571 | $C_2H_5$ | Cl | CH | NH | H | " | A | |
| 572 | " | " | " | " | " | " | B | |
| 573 | $CH_2OCH_3$ | $OCH_3$ | N | " | " | " | A | |
| 574 | $CH_2OCH3$ | $OCH_3$ | N | NH | H | 4-$CH_3O$—$C_6H_4$—$OCH_2$— | B | |
| 575 | $C_2H_5$ | Cl | " | " | " | 4-$C_2H_5O$—$C_6H_4$—$OCH_2$— | A | |
| 576 | $C_2H_5$ | Cl | N | NH | H | 4-$C_2H_5O$—$C_6H_4$—$OCH_2$— | B | |
| 577 | $C_2H_5$ | Cl | CH | NH | H | 4-$C_2H_5O$—$C_6H_4$—$OCH_2$— | A | |
| 578 | $C_2H_5$ | Cl | CH | NH | H | 4-$C_2H_5O$—$C_6H_4$—$OCH_2$— | B | |
| 579 | $CH_2OCH_3$ | $OCH_3$ | N | " | " | " | A | |
| 580 | " | " | " | " | " | " | B | |
| 581 | $C_2H_5$ | Cl | " | " | " | 3,4-$(CH_3O)_2$—$C_6H_4$—$OCH_2$— | A | |
| 582 | " | " | " | " | 3,4-$(CH_3O)_2$ $C_6H_4$ $OCH_2$— | " | B | |
| 583 | " | " | CH | " | " | 3,4-$(CH_3O)_2$—$C_6H_4$—$OCH_2$— | A | |
| 584 | " | " | " | " | " | 3,4-$(CH_3O)_2$—$C_6H_4$—$OCH_2$— | B | |
| 585 | $CH_2OCH_3$ | $OCH_3$ | N | " | " | 3,4-$(CH_3O)_2$—$C_6H_4$—$OCH_2$— | A | |
| 586 | " | " | " | " | " | 3,4-$(CH_3O)_2$—$C_6H_4$—$OCH_2$— | B | |
| 587 | $C_2H_5$ | Cl | " | " | " | 4-$C_6H_5O$—$C_6H_4$—$OCH_2$— | A | |
| 588 | " | " | " | " | " | " | B | |
| 589 | " | " | CH | " | " | " | A | |
| 590 | " | " | " | " | " | " | B | |
| 591 | $CH_2OCH_3$ | $OCH_3$ | N | " | " | " | A | |
| 592 | " | " | " | " | " | " | B | |
| 593 | $C_2H_5$ | Cl | " | " | " | 4-(4-acetyl-piperazin-1-yl)-phenoxymethyl | G | oil |
| 594 | $C_2H_5$ | Cl | N | NH | H | 4-(4-acetyl-piperazin-1-yl)-phenoxymethyl | B | |
| 595 | $C_2H_5$ | Cl | N | NH | H | benzyl | A | |
| 596 | " | " | " | " | " | " | B | |
| 597 | " | " | CH | " | " | " | A | |
| 598 | " | " | " | " | " | " | B | |
| 599 | $CH_2OCH_3$ | $OCH_3$ | N | " | " | " | A | |
| 600 | $CH_2OCH_3$ | $OCH_3$ | N | NH | H | benzyl | B | |
| 601 | $(CH_2)_4$ | | " | O | " | " | A | |
| 602 | " | | " | " | " | " | B | |

TABLE 5-continued

| Ex. No. | R² | R³ | A | X | R⁵ | R⁶ | Isomer | M.p. [°C.] |
|---|---|---|---|---|---|---|---|---|
| 603 | C₂H₅ | Cl | " | NH | " | 4-methylbenzyl | A | |
| 604 | " | " | " | " | " | " | B | |
| 605 | C₂H₅ | Cl | CH | NH | H | 4-methylbenzyl | A | |
| 606 | " | " | " | " | " | " | B | |
| 607 | " | " | N | " | " | 4-tert-butylbenzyl | A | |
| 608 | " | " | " | " | " | " | B | |
| 609 | " | " | CH | " | " | " | A | |
| 610 | " | " | " | " | " | " | B | |
| 611 | C₂H₅ | Cl | N | " | " | 4-fluorobenzyl | A | |
| 612 | " | " | " | " | " | " | B | |
| 613 | " | " | CH | " | " | " | A | |
| 614 | C₂H₅ | Cl | CH | NH | H | 4-fluorobenzyl | B | |
| 615 | " | " | N | " | " | 4-chlorobenzyl | A | |
| 616 | " | " | " | " | " | " | B | |
| 617 | " | " | CH | " | " | " | A | |
| 618 | " | " | " | " | " | " | B | |
| 619 | " | " | N | " | " | 4-methoxybenzyl | A | |
| 620 | " | " | " | " | " | " | B | |
| 621 | " | " | CH | " | " | " | A | |
| 622 | " | " | " | " | " | " | B | |
| 623 | C₂H₅ | Cl | N | NH | H | 4-ethoxybenzyl | A | |
| 624 | " | " | " | " | " | " | B | |
| 625 | " | " | CH | " | " | " | A | |
| 626 | " | " | " | " | " | " | B | |
| 627 | " | " | N | " | " | 3,4-dimethoxybenzyl | A | |
| 628 | " | " | " | " | " | " | B | |
| 629 | " | " | CH | " | " | " | A | |
| 630 | " | " | " | " | " | " | B | |
| 631 | CH₂OCH₃ | OCH₃ | N | " | " | " | A | |
| 632 | " | " | " | " | " | " | B | |
| 633 | C₂H₅ | Cl | N | NH | H | 4-trifluoromethyl-benzyl | A | |
| 634 | " | " | " | " | " | 4-trifluoromethyl-benzyl | B | |
| 635 | " | " | CH | " | " | 4-trifluoromethyl-benzyl | A | |
| 636 | " | " | " | " | " | 4-trifluoromethyl-benzyl | B | |
| 637 | C₂H₅ | Cl | N | NH | H | 4-CF₃—C₆H₄— | A | |
| 638 | " | " | " | " | " | " | B | |
| 639 | " | " | CH | " | " | " | A | |
| 640 | " | " | " | " | " | " | B | |
| 641 | " | " | N | " | " | 4-CF₃O—C₆H₄— | A | |
| 642 | " | " | " | " | " | " | B | |
| 643 | C₂H₅ | Cl | N | NH | H | Si(CH₃)₃— | A | |
| 644 | " | " | " | " | " | " | B | |
| 645 | " | " | CH | " | " | " | A | |
| 646 | C₂H₅ | Cl | CH | NH | H | Si(CH₃)₃ | B | |
| 647 | " | " | N | " | " | cyclopropyl | A | |
| 648 | " | " | " | " | " | " | B | |
| 649 | " | " | CH | " | " | " | A | |
| 650 | " | " | " | " | " | " | B | |
| 651 | " | " | N | " | " | cyclopentyl | A | |
| 652 | C₂H₅ | Cl | N | NH | H | cyclopentyl | B | |
| 653 | " | " | CH | " | " | " | A | |
| 654 | " | " | " | " | " | " | B | |
| 655 | " | " | N | " | " | cyclohexyl | A | |
| 656 | " | " | " | " | " | " | B | |
| 657 | " | " | CH | " | " | " | A | |
| 658 | " | " | " | " | " | " | B | |
| 659 | " | " | N | " | " | 6-methylpyrid-3-yl-oxymethyl | G | oil |

TABLE 6

| Ex. No. | R² | R³ | A | X | (R⁵)ₐ | R⁶ | Isomer | M.p. [°C.] |
|---|---|---|---|---|---|---|---|---|
| 700 | C₂H₅ | Cl | N | CH | H | CH₃ | A | |
| 701 | " | " | " | " | " | " | B | |
| 702 | " | " | CH | " | " | " | A | |
| 703 | " | " | " | " | " | " | B | |
| 704 | " | " | N | " | " | C₂H₅ | A | |
| 705 | " | " | " | " | " | " | B | |
| 706 | " | " | CH | " | " | " | A | |
| 707 | " | " | " | " | " | " | B | |
| 708 | " | " | N | " | " | n-C₃H₇ | A | |
| 709 | " | " | " | " | " | " | B | |
| 710 | " | " | CH | " | " | " | A | |
| 711 | " | " | " | " | " | " | B | |
| 712 | " | " | N | " | " | i-C₃H₇ | A | |
| 713 | " | " | " | " | " | " | B | |
| 714 | " | " | CH | " | " | " | A | |
| 715 | " | " | " | " | " | " | B | |
| 716 | " | " | N | " | " | n-C₄H₉ | A | |
| 717 | " | " | " | " | " | " | B | |
| 718 | C₂H₅ | Cl | CH | CH | H | n-C₄H₉ | A | |
| 719 | C₂H₅ | Cl | CH | CH | H | n-C₄H₉ | B | |
| 720 | " | " | N | " | " | tert-C₄H₉ | A | 117–119 |
| 721 | " | " | " | " | " | " | B | 103 |
| 722 | " | " | CH | " | " | " | A | |
| 723 | " | " | " | " | " | " | B | |
| 724 | " | " | N | NH | H | n-C₆H₁₃ | A | |
| 725 | C₂H₅ | Cl | N | NH | H | n-C₆H₁₃ | B | |
| 726 | " | " | CH | " | " | " | A | |
| 727 | " | " | " | " | " | " | B | |
| 728 | " | " | N | " | " | n-C₈H₁₇ | A | |
| 729 | " | " | " | " | " | " | B | |
| 730 | " | " | CH | " | " | " | A | |
| 731 | " | " | " | " | " | " | B | |
| 732 | " | " | N | " | 4,4-(CH₃)₂ | CH₃ | A | |
| 733 | " | " | " | " | " | " | B | |
| 734 | " | " | " | " | " | " | G | oil |
| 735 | " | " | " | " | H | C₆H₅ | A | 135–137 |
| 736 | C₂H₅ | Cl | N | NH | H | C₆H₅ | B | oil |
| 737 | " | " | CH | " | " | " | A | |
| 738 | " | " | " | " | " | " | B | |
| 739 | CH₂OCH₃ | OCH₃ | N | " | " | " | A | |
| 740 | " | " | " | " | " | " | B | |
| 741 | C₂H₅ | Cl | " | " | " | benzyl | A | |
| 742 | C₂H₅ | Cl | N | NH | H | benzyl | B | |
| 743 | " | " | CH | " | " | " | A | |
| 744 | " | " | " | " | " | " | B | |
| 745 | " | " | N | " | " | cyclopropyl | A | |
| 746 | " | " | " | " | " | " | B | |
| 747 | C₂H₅ | Cl | CH | " | H | " | A | |
| 748 | " | " | " | " | " | " | B | |
| 749 | " | " | N | " | " | cyclohexyl | A | |
| 750 | " | " | " | " | " | " | B | |
| 751 | " | " | CH | " | " | " | A | |
| 752 | " | " | " | " | " | " | B | |
| 753 | C₂H₅ | Cl | N | " | H | Si(CH₃)₃ | A | |
| 754 | C₂H₅ | Cl | N | " | H | Si(CH₃)₃ | B | |
| 755 | " | " | CH | " | " | " | A | |
| 756 | " | " | " | " | " | " | B | |
| 757 | " | " | N | " | " | —CH₂OCH₃ | G | oil |

TABLE 7

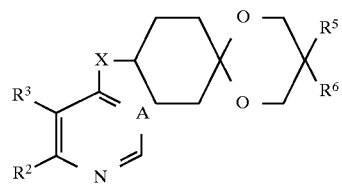

| Ex. No. | R² | R³ | A | X | R⁵ | R⁶ | M.p. [°C.] |
|---|---|---|---|---|---|---|---|
| 800 | C₂H₅ | Cl | N | NH | H | CH₃ | |
| 801 | " | " | CH | " | " | " | |
| 802 | CH₂OCH₃ | OCH₃ | N | " | " | " | |
| 803 | C₂H₅ | Cl | " | " | CH₃ | " | oil |
| 804 | CH₂OCH₃ | OCH₃ | " | " | " | " | 112–114 |
| 805 | C₂H₅ | Cl | CH | " | " | " | |
| 806 | " | " | N | O | " | " | 75 |
| 807 | CH₂OCH₃ | OCH₃ | " | " | " | " | oil |
| 808 | (CH₂)₄ | | " | " | " | " | 121 |
| 809 | C₂H₅ | Cl | " | NH | " | C₂H₅ | oil |
| 810 | " | " | CH | " | " | " | |
| 811 | " | " | N | O | " | " | oil |
| 812 | CH₂OCH₃ | OCH₃ | N | O | CH₃ | C₂H₅ | oil |
| 813 | " | " | " | NH | " | " | 98–99 |
| 814 | (CH₂)₄ | | " | O | " | " | 97–98 |
| 815 | C₂H₅ | Cl | " | NH | C₂H₅ | " | oil |
| 816 | " | " | CH | " | " | " | |
| 817 | " | " | N | O | " | " | oil |
| 818 | CH₂OCH₃ | OCH₃ | " | " | " | " | 46–47 |
| 819 | CH₂OCH₃ | OCH₃ | N | NH | C₂H₅ | " | 93–94 |
| 820 | C₂H₅ | Cl | N | " | CH₃ | n-C₃H₇ | |
| 821 | " | " | CH | " | " | " | |
| 822 | " | " | N | O | " | " | oil |
| 823 | CH₂OCH₃ | OCH₃ | " | NH | CH₃ | n-C₃H₇ | |
| 824 | " | " | " | O | " | " | |
| 825 | (CH₂)₄ | | N | O | CH₃ | n-C₃H₇ | |
| 826 | C₂H₅ | Cl | " | NH | H | n-C₄H₉ | |
| 827 | " | " | CH | " | " | " | |
| 828 | CH₂OCH₃ | OCH₃ | N | " | " | " | |
| 829 | C₂H₅ | Cl | " | " | " | tert-C₄H₉ | |
| 830 | " | " | CH | " | " | " | |
| 831 | CH₂OCH₃ | OCH₃ | N | NH | H | tert-C₄H₉ | |
| 832 | C₂H₅ | Cl | " | " | " | n-C₆H₁₃ | |
| 833 | " | " | CH | " | " | " | |
| 834 | CH₂OCH₃ | OCH₃ | N | " | " | " | |
| 835 | C₂H₅ | Cl | " | " | " | n-C₆H₁₇ | |
| 836 | " | " | CH | " | " | " | |
| 837 | CH₂OCH₃ | OCH₃ | N | " | " | " | |
| 838 | C₂H₅ | Cl | " | " | " | C₆H₅ | oil |
| 839 | " | " | CH | " | " | " | |
| 840 | CH₂OCH₃ | OCH₃ | N | " | " | " | |
| 841 | C₂H₅ | Cl | " | " | CH₃ | " | oil |
| 842 | C₂H₅ | Cl | CH | NH | CH₃ | C₆H₅ | |
| 843 | CH₂OCH₃ | OCH₃ | N | " | " | " | oil |
| 844 | C₂H₅ | Cl | " | " | H | CH₂C₆H₅ | |
| 845 | " | " | CH | " | " | " | |

TABLE 8

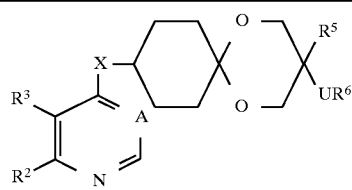

| Ex. No. | R² | R³ | A | X | R⁵ | U | R⁶ | M.p. [°C.] |
|---|---|---|---|---|---|---|---|---|
| 846 | CH₂OCH₃ | OCH₃ | N | NH | H | — | CH₂C₆H₅ | |
| 847 | C₂H₅ | Cl | " | " | H | O | CH₃ | |

TABLE 8-continued

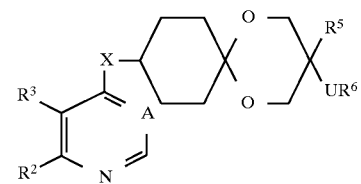

| Ex. No. | R² | R³ | A | X | R⁵ | U | R⁶ | M.p. [°C.] |
|---|---|---|---|---|---|---|---|---|
| 848 | " | " | CH | " | " | " | " | |
| 849 | CH₂OCH₃ | OCH₃ | N | " | " | " | " | |
| 850 | C₂H₅ | Cl | " | " | " | " | C₆H₅ | |
| 851 | " | " | CH | " | " | " | " | |
| 852 | CH₂OCH₃ | OCH₃ | N | " | " | " | " | |
| 853 | C₂H₅ | Cl | " | " | " | " | CH₂C₆H₅ | oil |
| 854 | " | " | CH | " | " | " | " | |
| 855 | CH₂OCH₃ | OCH₃ | N | " | " | " | " | oil |
| 856 | " | " | CH | " | CH₃ | — | CH₃ | oil |
| 857 | CH₃ | " | " | " | " | — | " | oil |

TABLE 9

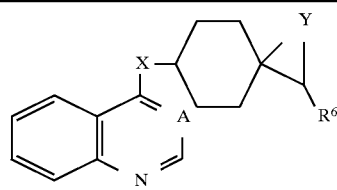

| Ex. No. | A | X | Y | R⁶ | Isomer | M.p.[°C.] |
|---|---|---|---|---|---|---|
| 900 | N | NH | CH₂ | H | — | |
| 901 | CH | " | " | " | — | |
| 902 | N | O | " | " | — | |
| 903 | CH | " | " | " | — | |
| 904 | N | NH | O | " | — | |
| 905 | CH | " | O | " | — | |
| 906 | N | O | O | " | — | |
| 907 | CH | " | O | " | — | |
| 908 | N | NH | CH₂ | CH₃ | A | |
| 909 | " | " | " | " | B | |
| 910 | " | " | O | " | A | |
| 911 | " | " | " | " | B | |
| 912 | " | " | CH₂ | C₂H₅ | A | |
| 913 | " | " | " | " | B | |
| 914 | " | " | O | " | A | |
| 915 | " | " | " | " | B | |
| 916 | " | " | CH₂ | n-C₃H₇ | A | |
| 917 | " | " | " | " | B | |
| 918 | " | " | O | " | A | |
| 919 | N | NH | O | n-C₃H₇ | B | |
| 920 | " | " | CH₂ | i-C₃H₇ | A | |
| 921 | " | " | " | " | B | |
| 922 | " | " | O | " | A | |
| 923 | " | " | " | " | B | |
| 924 | N | NH | CH₂ | n-C₄H₉ | A | |
| 925 | N | NH | CH₂ | n-C₄H₉ | B | |
| 926 | CH | " | " | " | A | |
| 927 | " | " | " | " | B | |
| 928 | N | O | " | " | A | |
| 929 | " | " | " | " | B | |
| 930 | CH | " | " | " | A | |
| 931 | " | " | " | " | B | |
| 932 | N | NH | O | " | A | |
| 933 | " | " | " | " | B | |
| 934 | CH | " | " | " | A | |
| 935 | " | " | " | " | B | |
| 936 | N | O | " | " | A | |
| 937 | " | " | " | " | B | |
| 938 | CH | " | " | " | A | |
| 939 | CH | O | O | n-C₄H₉ | B | |

TABLE 9-continued

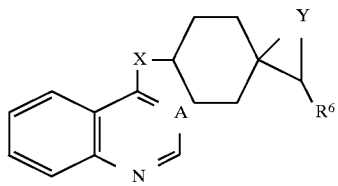

| Ex. No. | A | X | Y | R6 | Isomer | M.p.[°C.] |
|---|---|---|---|---|---|---|
| 940 | N | NH | CH2 | tert-C4H9 | A | |
| 941 | " | " | " | " | B | |
| 942 | N | NH | O | tert-C6H9 | A | |
| 943 | " | " | " | " | B | |
| 944 | " | " | CH2 | n-C8H17 | A | |
| 945 | " | " | " | " | B | |
| 946 | " | " | O | " | A | |
| 947 | " | " | " | " | B | |
| 948 | N | NH | CH2 | C6H5 | A | |
| 949 | " | " | " | " | B | |
| 950 | CH | " | " | " | A | |
| 951 | " | " | " | " | B | |
| 952 | N | O | " | " | A | |
| 953 | " | " | " | " | B | |
| 954 | CH | " | " | " | A | |
| 955 | " | " | " | " | B | |
| 956 | N | NH | O | " | A | |
| 957 | " | " | " | " | B | |
| 958 | CH | NH | O | C6H5 | A | |
| 959 | CH | NH | O | C6H5 | B | |
| 960 | N | O | " | " | A | |
| 961 | " | " | " | " | B | |
| 962 | CH | " | " | " | A | |
| 963 | " | " | " | " | B | |
| 964 | N | NH | CH2 | benzyl | A | |
| 965 | N | NH | CH2 | benzyl | B | |
| 966 | " | " | O | " | A | |
| 967 | " | " | " | " | B | |
| 968 | " | " | CH2 | 2-thienyl | A | |
| 969 | " | " | " | " | B | |
| 970 | " | " | O | " | A | |
| 971 | " | " | " | " | B | |

TABLE 10

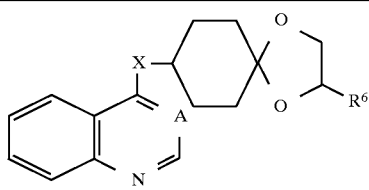

| Ex. No. | A | X | R6 | Isomer | M.p. [°C.] |
|---|---|---|---|---|---|
| 1000 | N | NH | CH3 | A | |
| 1001 | " | " | " | B | |
| 1002 | " | " | C2H5 | A | |
| 1003 | " | " | " | B | |
| 1004 | " | " | n-C3H7 | A | |
| 1005 | " | " | " | B | |
| 1006 | " | " | i-C3H7 | A | |
| 1007 | " | " | " | B | |
| 1008 | " | " | n-C4H9 | A | |
| 1009 | " | " | " | B | |
| 1010 | CH | " | " | A | |
| 1011 | " | " | " | B | |
| 1012 | " | O | " | A | |
| 1013 | " | " | " | B | |
| 1014 | N | " | " | A | |
| 1015 | " | " | " | B | |
| 1016 | " | NH | tert-C4H9 | A | |
| 1017 | " | " | " | B | |
| 1018 | CH | " | " | A | |

TABLE 10-continued

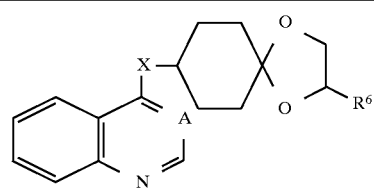

| Ex. No. | A | X | R6 | Isomer | M.p. [°C.] |
|---|---|---|---|---|---|
| 1019 | CH | NH | tert-C4H9 | B | |
| 1020 | " | O | " | A | |
| 1021 | " | " | " | B | |
| 1022 | N | O | tert-C4H9 | A | |
| 1023 | " | " | " | B | |
| 1024 | N | NH | n-C6H13 | A | |
| 1025 | " | " | " | B | |
| 1026 | " | " | n-C8H17 | A | |
| 1027 | " | " | " | B | |
| 1028 | " | " | C6H5 | A | |
| 1029 | " | " | " | B | |
| 1030 | CH | " | " | A | |
| 1031 | " | " | " | B | |
| 1032 | N | O | " | A | |
| 1033 | " | " | " | B | |
| 1034 | CH | " | " | A | |
| 1035 | " | " | " | B | |
| 1036 | N | NH | benzyl | A | |
| 1037 | " | " | " | B | |
| 1038 | N | NH | 2-thienyl | A | |
| 1039 | " | " | " | B | |
| 1040 | " | " | CH2—OCH3 | A | |
| 1041 | " | " | " | B | |
| 1042 | N | NH | C2H5—OCH2— | A | |
| 1043 | " | " | " | B | |
| 1044 | " | O | " | A | |
| 1045 | " | " | " | B | |
| 1046 | " | " | " | G | oil |
| 1047 | " | NH | tert-C4H9OCH2 | A | |
| 1048 | N | NH | tert-C4H9OCH2 | B | |
| 1049 | N | O | C2H5OCH2— | G | oil |
| 1050 | " | " | tert-C4H9OCH2— | G | oil |

TABLE 11

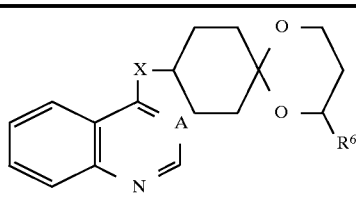

| Ex. No. | A | X | R6 | Isomer | m.p. [°C.] |
|---|---|---|---|---|---|
| 1051 | N | NH | n-C4H9 | A | |
| 1052 | " | " | " | B | |
| 1053 | " | " | tert-C4H9 | A | |
| 1054 | " | " | " | B | |
| 1055 | CH | " | " | A | |
| 1056 | " | " | " | B | |
| 1057 | N | " | n-C8H17 | A | |
| 1058 | " | " | " | B | |
| 1059 | " | " | C6H5 | A | |
| 1060 | " | " | " | B | |
| 1061 | CH | " | " | A | |
| 1062 | " | " | " | B | |

TABLE 12

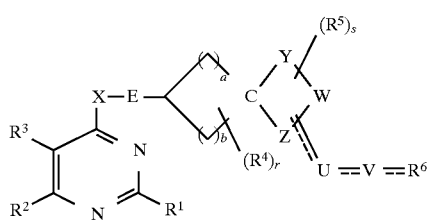

| Ex. No. | A | X | $R^5$ | $R^6$ | M.p. [°C.] |
|---|---|---|---|---|---|
| 1063 | N | NH | $CH_3$ | $CH_3$ | |
| 1064 | " | O | " | " | 121 |
| 1065 | " | NH | " | $C_2H_5$ | |
| 1066 | " | O | " | " | 62–63 |
| 1067 | " | NH | " | $n\text{-}C_3H_7$ | |
| 1068 | " | O | " | " | oil |
| 1069 | " | NH | $C_2H_5$ | $C_2H_5$ | |
| 1070 | " | O | " | " | 92–94 |
| 1071 | " | NH | H | $C_6H_5$ | |
| 1072 | " | O | " | " | |
| 1073 | " | NH | $CH_3$ | " | |
| 1074 | " | O | " | " | |

We claim:

1. A compound of the formula I

in which $R^1$ is hydrogen, halogen, $(C_1-C_4)$-alkyl, $(C_1-C_4)$-haloalkyl, $(C_3-C_5)$-cycloalkyl or $(C_3-C_5)$-halocycloalkyl;

$R^2$ and $R^3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, tri$(C_1-C_4)$-alkylsilyl-$(C_2-C_4)$-alkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl; or $R^2$ and $R^3$ together with the carbon atoms to which they are bonded form an unsaturated 5- or 6-membered carbocyclic ring which, if it is a 5-membered ring, optionally contains an oxygen or sulfur atom in place of $CH_2$ or which, if it is a 6-membered ring, optionally contains one or two nitrogen atoms in place of one or two CH units, and which is optionally substituted by 1, 2 or 3 identical or different radicals, these radicals being $(C_1-C_4)$-alkyl, $(C_1-C_4)$-haloalkyl, halogen, $(C_1-C_4)$-alkoxy or $(C_1-C_4)$-haloalkoxy, or $R^2$ and $R^3$ together with the carbon atoms to which they are bonded form a saturated 5-, 6- or 7-membered carbocyclic ring which contains oxygen and/or sulfur in place of one or two $CH_2$ groups and which is optionally substituted by 1, 2 or 3 $(C_1-C_4)$-alkyl groups;

X is NH, oxygen or $S(O)_q$ where q is 0, 1 or 2;

E is a direct bond or a straight-chain or branched $(C_1-C_4)$ alkanediyl group;

Y and Z are identical or different and independently of one another are in each case $CH_2$, oxygen or a group $S(O)_x$ where x is 0, 1 or 2;

W is a group $(CH_2)_n$ where n is an integer from 1 to 4, or

W, in the event that Y and/or Z are $CH_2$, is optionally a direct bond between Y and Z; one or more hydrogen atoms in the group —Y—W—Z— are optionally replaced by =U=V=$R^6$ and, optionally, by $R^5$, as shown in formula I and described hereinbelow;

a and b are identical or different and independently of one another are the numbers 0, 1, 2 or 3, a and b not simultaneously being 0;

$R^4$ and $R^5$ are identical or different and independently of one another are in each case halogen, $(C_2-C_{20})$-alkyl, haloalkyl, alkoxy, haloalkoxy or alkylthio;

r and s are identical or different and independently of one another are 0, 1 or 2;

U is a single bond, oxygen, a group $S(O)_y$ where y is 0, 1 or 2 or a croup $NR^7$ where $R^7$ is hydrogen, $(C_1-C_4)$-alkyl or $(C_1-C_4)$-alkoxy;

V is a single bond, carbonyl or a group of the formula $$-\underset{\underset{Q}{\|}}{C}-T-$$

or

where Q is oxygen, sulfur or $(C_1-C_4)$-alkylimino, T is oxygen, sulfur or a group $NR^{7'}$, and T' is $(C_1-C_4)$-alkoxy, $(C_1-C_4)$-alkylthio or $NR^{7'} R^{7''}$, and where $R^{7'}$ and $R^{7''}$ are identical or different and are as defined above for $R^7$; or U and V together are a double bond; and
 a) $R^6$ is $(C_2-C_{20})$-alkyl, alkenyl, alkynyl, optionally substituted aryl, optionally substituted heterocyclyl or cyano, or, in the event that U and V together are a direct single bond,
 b) $R^6$ is as defined above or is halogen, hydroxyl, carboxyl, nitro or a group $SiR^8R^9R^{10}$ where $R^8$ and $R^9$ are $(C_1-C_4)$-alkyl and $R^{10}$ is alkyl or optionally substituted aryl, or, in the event that U and V together are a double bond,
 c) $R^6$ is alkylidene or alkyloximino; and the alkyl, alkenyl, alkynyl, alkylidene or alkyloximino radicals mentioned under a), b) or c) for $R^6$, $R^8$, $R^9$ and $R^{10}$ have at least one of the following characteristics:
  i. one or more non-adjacent $CH_2$ groups are replaced by CO and/or heteroatom units selected from the group consisting of O, $S(O)_x$, $NR^{11}$, and $SiR^{12}R^{13}$ wherein x is 0, 1, or 2, $R^{11}$ is H, $(C_1-C_4)$alkyl, $(C_1-C_4)$alkoxy, or $(C_1-C_4)$alkanoyl; $R^{12}$ and $R^{13}$ are $(C_1-C_4)$alkyl;
  ii. 3 to 8 atoms of these radicals form an up to 8-membered ring;

iii. the hydrocarbon radicals, with or without the abovementioned variations, are optionally substituted by one or more, identical or different radicals selected from the group consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocycloylalkanoyloxy, alkylsulfonyloxy, arylsulfonyloxy, hydroxyl, cyano, thiocyano or nitro, wherein said cycloaliphatic, aromatic or heterocyclic ring systems in the substituents which have just been mentioned are unsubstituted or substituted with up to three, in the case of halogen, also up to the maximum number of, identical or different substituents;

and furthermore, in the event that $R^5$ and $R^6$ are alkyl radicals, these variables are optionally linked cyclically or spirocyclically;

with the exception of those compounds of formula I, wherein $R^1$ is hydrogen; $R^3$ is $CH_2OCH_3$; $R^3$ is $OCH_3$; X is NH; E is a direct bond; and Q is

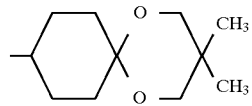

wherein heterocycle, if not further specified, means a heteroaromatic system selected from the group consisting of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine, 4H-quinolizine or a $(C_3-C_8)$-cycloalkyl radical in which at least one carbon unit is replaced by O, S or a group $NR^{14}$ and $R^{14}$ is hydrogen, $(C_1-C_4)$-alkyl, $(C_1-C_4)$-alkoxy or aryl; and wherein substituted, if not further specified is selected from the group consisting of halogen, nitro, cyano, di-$(C_1-C_4)$-alkylamino, $(C_1-C_4)$-alkyl, $(C_3-C_8)$-cycloalkyl, $(C_1-C_4)$-trialkylsilyl, $(C_1-C_4)$-alkoxy, $(C_1-C_4)$-alkoxy-$(C_1-C_4)$-alkyl, $(C_1-C_2)$-alkoxy-$[CH_2CH_2O]_{1,2}$-ethoxy, $(C_1-C_4)$-alkylthio, $(C_1-C_4)$-alkylsulfinyl, $(C_1-C_4)$-alkyl-sulfonyl, thiocyano, $(C_1-C_4)$-haloalkyl, $(C_1-C_4)$-haloalkoxy, $(C_1-C_4)$-haloalkylthio, $(C_2-C_4)$-haloalkylsulfinyl, $(C_1-C_4)$-haloalkylsulfonyl, $(C_2-C_4)$-alkenyl, $(C_2-C_4)$-haloalkenyl, trimethylsilylethynyl, $(C_1-C_4)$-alkanoyl, $(C_1-C_4)$-alkoxycarbonyl, 4-acetylpiperanzin-1-yl, phenyl, benzyl, phenoxy, halophenoxy, $(C_1-C_4)$-alkylphenoxy, $(C_1-C_4)$-alkoxyphenoxy, phenylthio, heterocyclyl, heterocyclylthio or heterocyclyloxy, it being possible for one or more hydrogen atoms, in the case of fluorine also up to the maximum number of hydrogen atoms, in the alkyl radicals and the radicals derived therefrom to be replaced by halogen or a salt thereof.

2. A compound of the formula I as claimed in claim 1, in which $R^4$ and $R^5$ are halogen, $C_2-C_4$)-alkyl, $(C_1-C_4)$-haloalkyl, $(C_1-C_4)$-alkoxy, $(C_1-C_4)$-haloalkoxy or $(C_1-C_4)$-alkylthio; and a) $R^6$ is $C_2-C_{20}$)-alkyl, $(C_2-C_{20})$-alkenyl, $(C_2-C_{20})$-alkynyl, optionally substituted aryl, optionally substituted heterocyclyl or cyano, or, in the event that U and V together are a single bond, b) $R^6$ is as defined above or is halogen, hydroxyl, carboxyl, nitro or a group $SiR^8R^8R^{10}$ where $R^8$ and $R^9$ are $(C_1-C_4)$-alkyl and $R^{10}$ is $(C_1-C_{20})$-alkyl or optionally substituted aryl, or in the event that U and V together are a double bond, i. one or more non-adjacent $CH_2$ groups are replaced by CO and/or heteroatom units;

ii. 3 to 6 atoms of these radicals form an up to 6-membered ring;

iii. the hydrocarbon radicals, with or without the abovementioned variations, are optionally substituted by one or more identical or different radicals selected from the group consisting of halogen, aryl, aryloxy, arylthio, $(C_3-C_8)$-cycloalkoxy, $(C_3-C_8)$-cycloalkylthio, heterocyclyl, heterocyclyloxy, heterocyclylthio, $(C_1-C_{12})$-alkanoyl, $(C_3-C_8)$-cycloalkanoyl, $(C_2-C_{12})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{12})$-alkoxycarbonyl, $(C_1-C_{12})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{12})$-alkanoyloxy, $(C_2-C_{12})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{12})$-alkylsulfonyloxy, arylsulfonyloxy, hydroxyl, cyano, thiocyano or nitro, wherein said cycloaliphatic, aromatic or heterocyclic ring systems amongst the substituents which have just been mentioned are unsubstituted or substituted with up to three, in the case of halogen also up to the maximum number of, identical or different substituents, and, in the event that $R^5$ and $R^6$ are alkyl radicals, it furthermore is possible for these variables to be cyclically or spirocyclically linked, and the remaining radicals and variables are as defined in claim 1, or a salt thereof.

3. A compound of the formula I as claimed in claim 1, in which $R^1$ is hydrogen, chlorine or fluorine;

$R^2$ is $(C_1-C_4)$-alkyl, $(C_1-C_4)$-haloalkyl, $(C_2-C_4)$-alkenyl, $(C_2-C_4)$-alkynyl, trimethylsilylethynyl, $(C_2-C_4)$-haloalkenyl, cyclopropyl, halocyclopropyl, methoxymethyl or cyano;

$R^3$ is hydrogen, halogen, methyl, ethyl, ($C_2$–$C_4$)-alkenyl, ($C_2$–$C_4$)-alkynyl, trimethylsilylethynyl, ($C_2$–$C_4$)-haloalkzenyl, methoxy, ethoxy, cyano or ($C_1$–$C_4$)-alkoxycarbonyl; or $R^2$ and $R^3$ together with the carbon atoms to which they are bonded form an optionally substituted unsaturated 5- or 6-membered carbocyclic ring which, in the event of a 5-membered ring, optionally contains a sulfur atom in place of a $CH_2$ unit, or $R^2$ and $R^3$ together with the carbon atoms to which they are bonded form a saturated 5- or 6-membered carbocyclic ring which optionally contains a sulfur or an oxygen atom in place of a $CH_2$ unit;

X is NH or oxygen;

E is a direct bond;

Y and Z are identical or different and are in each case $CH_2$, oxygen or sulfur, and the group —Y—W—Z— is substituted as described above;

a and b are in each case the number 2, $R^4$ and $R^5$ are identical or different and are in each case $C_2$–$C_4$-alkyl, trifluoromethyl or ($C_1$–$C_4$)-alkoxy; and the remaining radicals and variables are as defined in claim 1;

or a salt thereof.

4. A compound of the formula I as claimed in claim 1, in which $R^1$ is hydrogen or fluorine;

$R^2$ is methyl, ethyl, propyl, isopropyl, ($C_1$–$C_2$)-fluoroalkyl, ethynyl, trimethylsilylethynyl, cyclopropyl or methoxymethyl;

$R^3$ is halogen, methyl, ethyl, ethynyl, trimethylsilylethynyl, methoxy, ethoxy or cyano, or $R^2$ and $R^3$ together with the ring system to which they are bonded form the quinazoline system which are optionally substituted in the carbocyclic moiety by fluorine, or $R^2$ and $R^3$ together with the carbon atoms to which they are bonded form a saturated 6-membered carbocyclic ring which optionally contains an oxygen or sulfur atom in place of a $CH_2$ group;

Y and Z are identical or different and are in each case $CH_2$ or oxygen and the group —Y—W—Z— is substituted as described above;

r is 0;

$R^5$ is trifluoromethyl;

U is a direct bond or oxygen;

V is a direct bond; or

U and V together are a double bond; and the remaining radicals and variables are as defined in claim 1;

or a salt thereof.

5. A compound of the formula I as claimed in claim 1, in which $R^1$ is hydrogen;

$R^2$ is ethyl, propyl, isopropyl, 1-fluoroethyl, ethynyl, trimethylsilylethynyl, trifluoromethyl or methoxymethyl, $R^3$ is fluorine, chlorine, bromine, ethynyl, trimethylsilylethynyl or methoxy; or $R^2$ and $R^3$ together with the ring system to which they are bonded form the quinazoline system which is optionally substituted by a fluorine atom, or $R^2$ and $R^3$ together with the ring system to which they are bonded form the 5,6,7,8-tetrahydroquinazoline system;

X is NH or oxygen;

E is a direct bond;

Y and Z are identical or different and are in each case $CH_2$ or oxygen;

W is a group $(CH_2)_n$ where n is 2 or 3, or

W, in the event that Y and/or Z are $CH_2$, is optionally a direct bond between Y and Z; and one or more hydrogen atoms in the group —Y—W—Z— are optionally replaced by =U=V=$R^6$ and, optionally, by $R^5$, as shown in formula I and described above;

a and b are the number 2;

r is 0;

s is 0, 1 or 2;

$R^5$ is ethyl;

U is a single bond or oxygen,

V is a single bond;

and the remaining radicals are as defined in claim 1;

or a salt thereof.

6. A compound of the formula I as claimed in claim 1, in which

Y is $CH_2$;

Z is $CH_2$ or oxygen, and, in this case,

W is a direct bond between Y and Z;

or Y and Z are oxygen and, in this case,

W is a group $(CH_2)_n$ and n is a number 2 or 3;

U and V together are a single bond; and the remaining radicals and variables are as defined in claim 1;

or a salt thereof.

7. A compound of the formula I as claimed in claim 1, in which $R^1$ is hydrogen;

$R^2$ is ethyl or methoxymethyl;

$R^2$ and $R^3$ together with the ring system to which they are bonded form the quinazoline or the 5,6,7,8-tetrahydroquinazoline system;

X is NH or oxygen;

a and b are in each case 2, and r and s are in each case 0;

E is a direct bond;

Y is $CH_2$ and

Z is $CH_2$ or oxygen,

U and V together are a direct single bond; and in this case

W is a direct bond between Y and Z, or Y and Z are in each case oxygen, and in this case W is a group $(CH_2)_n$ which is optionally substituted as described above and n is a number 2 or 3;

r and s are in each case 0;

$R^6$ is ($C_2$–$C_{20}$)-alkyl, ($C_2$–$C_{20}$)-alkenyl, ($C_2$–$C_{20}$)-alkynyl, optionally substituted aryl or optionally substituted heterocyclyl, and wherein one or more non-adjacent $CH_2$ groups in the abovementioned alkyl, alkenyl or alkynyl radicals are optionally replaced by oxygen or sulfur, and, wherein 3 to 6 atoms of these alkyl, alkenyl or alkynyl radicals, with or without the abovementioned variations, optionally form a carbocyclic ring, and wherein these alkyl, alkenyl or alkynyl radicals, with or without the abovementioned variations including the ring, are optionally substituted by one, or in the case of halogen up to the maximum number of, radicals selected from the group consisting of halogen, aryl, aryloxy, arylthio, heterocyclyl, heterocyclyloxy, heterocyclylthio or hydroxyl; and the remaining radicals and variables are as defined in claim 1;

or a salt thereof.

8. A compound of the formula I as claimed in claim 1, in which
R² is methoxymethyl and R³ is methoxy, or
R² is ethyl and R³ is chlorine or bromine;
X is NH;
Y and Z are oxygen;
W is a group (CH₂)ₙ which is optionally substituted as described above and n is the number 2;
R⁶ is (C₂–C₂₀)-alkyl, aryl or heterocyclyl, all of which are optionally substituted, and optionally one or more non-adjacent CH₂ groups in the abovementioned alkyl radical are replaced by oxygen or sulfur, and wherein 3 to 6 atoms, with or without the abovementioned substitution, optionally form a ring; and the remaining radicals and variables are as defined in claim 1;
or a salt thereof.

9. A process for the preparation of compounds of the formula I as claimed in claim 1, which comprises
a) reacting a compound of the formula II

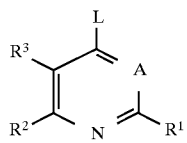
(II)

in which A is N and R¹, R² and R³ are as defined for formula I and L is a leaving group, with a compound of the formula III
in which a, b, r, s, E, U, V, W, X, Y, Z, R⁴, R⁵ and

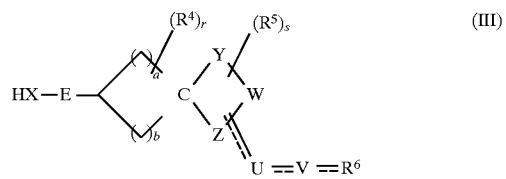
(III)

R⁶ are as defined for formula I;
b) to prepare compounds of the formula I in which Y and Z are oxygen and W is a group (CH₂)ₙ in which n is 2, 3 or 4, reacting, in the presence of an acid catalyst, a compound of the formula IV

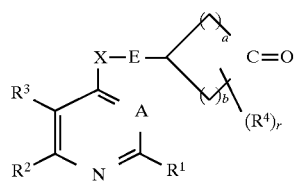
(IV)

in which a, b, r, A, X, E, R¹, R², R³ and R⁴ are as defined for formula I with a diol of the formula V

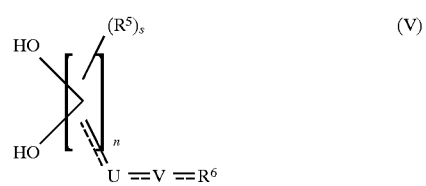
(V)

in which U, V, R⁵, R⁶ and s are as defined above and n is a number 2, 3 or 4;
c) to prepare compounds of the formula I in which Y and Z are oxygen and W is a group (CH₂)ₙ in which n is 2, 3 or 4, reacting, in the presence of an acid catalyst, a compound of the formula I'

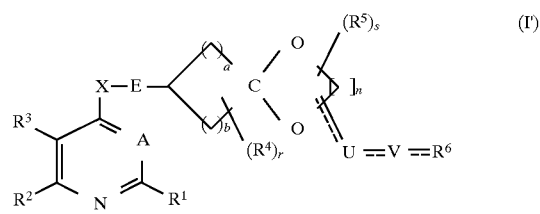
(I')

in which R¹, R², R³, R⁴, R⁵, R⁶, a, b, r, s, A, X, U, V and E are as defined for formula I, n is 2, 3 or 4, with a diol of the formula V defined above under b), with ketal exchange provided that at least one of R⁵, s, n, U, V or R⁶ is different in formula (I) than in formula (I') and, optionally, converting the resulting compounds of the formula I into their salts.

10. A fungicidal composition which comprises a fungicidally effective amount of at least one compound as claimed in claim 1 together with the additives or auxiliaries conventionally used for this application.

11. An insecticidal, acairicidal, ixodicidal or nematicidal composition, which comprises an effective amount of at least one compound as claimed in claim 1 together with the additives or auxiliaries conventionally used for this application.

12. A crop protection composition which comprises a fungicidally, insecticidally, acaricidally, ixodicidally or nematicidally effective amount of one or more compound as claimed in claim 1 and of one or more further active substance, selected from the group of the fungicides, insecticides, attractants, sterilants, acaricides, nematicides and herbicides, together with the auxiliaries and additives conventionally used for this application.

13. A composition for use in the protection of wood or as a preservative in sealing compositions, in paints, in cooling lubricants for metal working or in drilling and cutting oils, which comprises an effective amount of at least one compound as claimed in claim 1 together with the auxiliaries and additives conventionally used for these applications.

14. A composition for controlling endo- or ectoparasites which comprises an amount of a compound as claimed in claim 1 which is effective for this application, and a physiologically acceptable carrier.

15. A method of controlling endo- and ectoparasites, which comprises administering an effective amount of a compound as claimed in claim 1.

16. A method of controlling phytopathogenic fungi, which comprises applying a fungicidally effective amount of a compound as claimed in claim 1 to these phytopathogenic fungi or to the plants, areas or substrates or seed infested with them.

17. A method of controlling insect pests, acarina, mollusks and nematodes, in which an effective amount of a compound as claimed in claim 1 is applied to these insect pests, acarina, mollusks and nematodes or to the plants, areas or substrates infested with them.

18. A method for protecting wood, wherein the wood is treated with active amount of a compound as claimed in claim 1.

19. A method for the preservation of sealing compositions, paints, cooling lubricants for metalworking, drilling and cutting oils, wherein they are treated with an effective amount of a compound as claimed in claim 1.

20. Seed, treated or coated with an effective amount of a compound as claimed in claim 1.

* * * * *

UNITED STATES PATENT AND TRADEMARK OFFICE
CERTIFICATE OF CORRECTION

PATENT NO. : 5,859,009              Page 1 of 2
DATED      : January 12, 1999
INVENTOR(S): Schaper, et al.

It is certified that error appears in the above-identified patent and that said Letters Patent is hereby corrected as shown below:

In Column 2, line 35 of the Patent, replace "-C-N-" with -- -C=N- --.
                                                $\phantom{xx}|\phantom{xxxxxxxxx}|$
                                                $\phantom{xx}$T$\phantom{xxxxxxxxx}$T IN THE CLAIMS:
  In Claim 1, col. 62, line 38 of the Patent, replace "-C-N-" with -- -C=N- --.
                                                     $\phantom{xx}|\phantom{xxxxxxxxx}|$
                                                     $\phantom{xx}$T$\phantom{xxxxxxxxx}$T In Claim 2, col. 64, line 13, of the Patent, replace "$C_2$-$C_4$)-alkyl" with -- ($C_2$-$C_4$)-alkyl --.

In Claim 2, col. 64, line 16 of the Patent, replace "$C_2$-$C_{20}$)-alkyl" with -- ($C_2$-$C_{20}$)-alkyl --.

In Claim 3, col. 65, line 3 of the Patent, replace "haloalkzenyl" with --

-- haloalkenyl --.

In Claim 3, col. 65. line 22 of thePatent, replace "$C_2$-$C_4$)-alkyl" with

-- ($C_2$-$C_4$)-alkyl --.

UNITED STATES PATENT AND TRADEMARK OFFICE
CERTIFICATE OF CORRECTION

PATENT NO.  : 5,859,009
DATED       : Jan. 12, 1999
INVENTOR(S) : Schaper, et al It is certified that error appears in the above-identified patent and that said Letters Patent is hereby corrected as shown below:

In Claim 11, col. 68, line 23 of the Patent, replace "acairicidal" with

-- acaricidal --.

Signed and Sealed this

Tenth Day of August, 1999

*Attest:*

Q. TODD DICKINSON

*Attesting Officer*         *Acting Commissioner of Patents and Trademarks*